US012594000B2

(12) United States Patent
  Romoscanu

(10) Patent No.: US 12,594,000 B2
(45) Date of Patent: Apr. 7, 2026

(54) CARDIAC CATHETER WITH DEFORMABLE BODY

(71) Applicant: St. Jude Medical International Holding S.á r.l., Luxembourg (LU)

(72) Inventor: Alexandre Romoscanu, Geneva (CH)

(73) Assignee: St. Jude Medical International Holding S.á r.l., Luxembourg (LU)

( * ) Notice: Subject to any disclaimer, the term of this patent is extended or adjusted under 35 U.S.C. 154(b) by 866 days.

(21) Appl. No.: 16/483,620

(22) PCT Filed: Feb. 6, 2018

(86) PCT No.: PCT/IB2018/050732
  § 371 (c)(1),
  (2) Date: Aug. 5, 2019

(87) PCT Pub. No.: WO2018/142372
  PCT Pub. Date: Aug. 9, 2018

(65) Prior Publication Data
  US 2020/0093396 A1    Mar. 26, 2020

Related U.S. Application Data

(60) Provisional application No. 62/541,805, filed on Aug. 7, 2017, provisional application No. 62/455,048, filed on Feb. 6, 2017.

(51) Int. Cl.
  *A61B 5/00*    (2006.01)
  *A61B 5/06*    (2006.01)
  *A61B 18/14*    (2006.01)
  *A61B 18/00*    (2006.01)

(52) U.S. Cl.
  CPC ........... *A61B 5/062* (2013.01); *A61B 5/6852* (2013.01); *A61B 5/6885* (2013.01); *A61B 18/1492* (2013.01); *A61B 2018/00351* (2013.01); *A61B 2018/00577* (2013.01); *A61B 2018/00773* (2013.01); *A61B 2218/002* (2013.01); *A61B 2562/0223* (2013.01)

(58) Field of Classification Search
  CPC ... A61B 5/062; A61B 5/6852; A61B 18/1492; A61B 2018/00577; A61B 2018/00773; A61B 2562/0223
  See application file for complete search history.

(56) References Cited

U.S. PATENT DOCUMENTS

| | | | |
|---|---|---|---|
| 8,048,063 B2 | 11/2011 | Aeby et al. | |
| 2005/0076914 A1* | 4/2005 | Besharim ............ | A61M 16/049 128/207.14 |

(Continued)

*Primary Examiner* — Keith M Raymond
*Assistant Examiner* — Adam D. Kolkin
(74) *Attorney, Agent, or Firm* — DENTONS Durham Jones Pinegar

(57) ABSTRACT

Aspects of the instant disclosure relate to various types of medical catheters with a deformable body that deflect in response to a force exerted on the catheter tip. A magnetic field sensor and permanent magnet respectively coupled on either side of the deformable body are used to determine a change in a magnetic field associated with the deflection of the catheter tip. Controller circuitry may receive a signal from the magnetic field sensor indicative of the deflection of the deformable body and associate the signal with the force exerted.

22 Claims, 18 Drawing Sheets

(56)         References Cited

U.S. PATENT DOCUMENTS

| 2009/0093806 A1* | 4/2009 | Govari | A61B 18/1492 |
| | | | 606/34 |
| 2011/0015533 A1* | 1/2011 | Cox | A61B 5/283 |
| | | | 600/509 |
| 2012/0071927 A1* | 3/2012 | Beger | A61B 17/7026 |
| | | | 606/255 |
| 2012/0153942 A1* | 6/2012 | van Veldhoven | G01R 33/0017 |
| | | | 324/252 |
| 2012/0253167 A1 | 10/2012 | Bonyak et al. | |
| 2012/0259194 A1 | 10/2012 | Selkee | |
| 2012/0302820 A1* | 11/2012 | Carmeli | A61B 5/0538 |
| | | | 600/12 |
| 2014/0206953 A1 | 7/2014 | Valdastri | |
| 2015/0011993 A1* | 1/2015 | Horlle | A61B 18/1492 |
| | | | 606/41 |
| 2015/0216550 A1 | 8/2015 | Richter et al. | |
| 2016/0100860 A1* | 4/2016 | Lenker | A61B 17/3478 |
| | | | 604/95.01 |
| 2016/0228180 A1 | 8/2016 | Sliwa et al. | |
| 2016/0278852 A1 | 9/2016 | Sliwa et al. | |
| 2016/0345857 A1 | 12/2016 | Jensrud et al. | |
| 2016/0367217 A1* | 12/2016 | Flores | A61B 8/0808 |

* cited by examiner

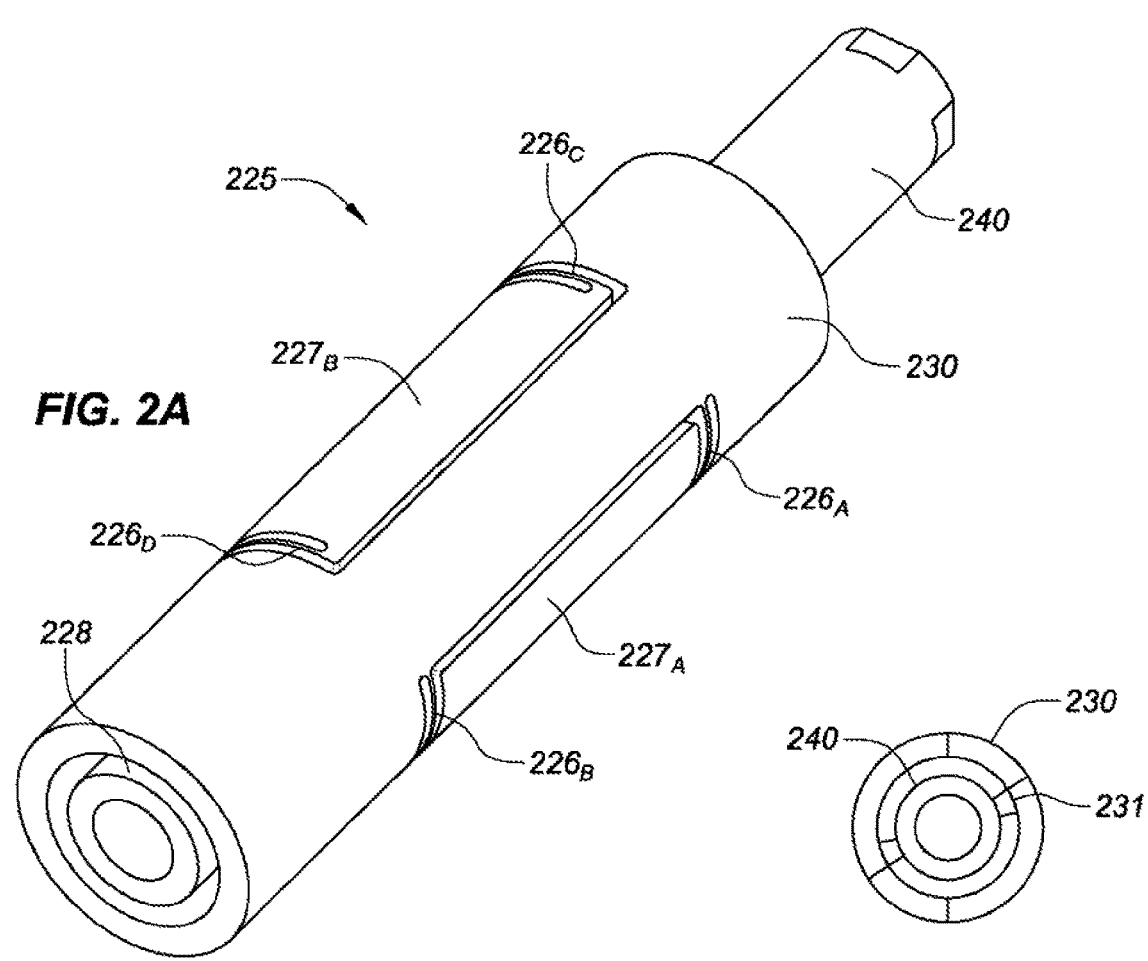
*FIG. 2A*
*FIG. 2B*
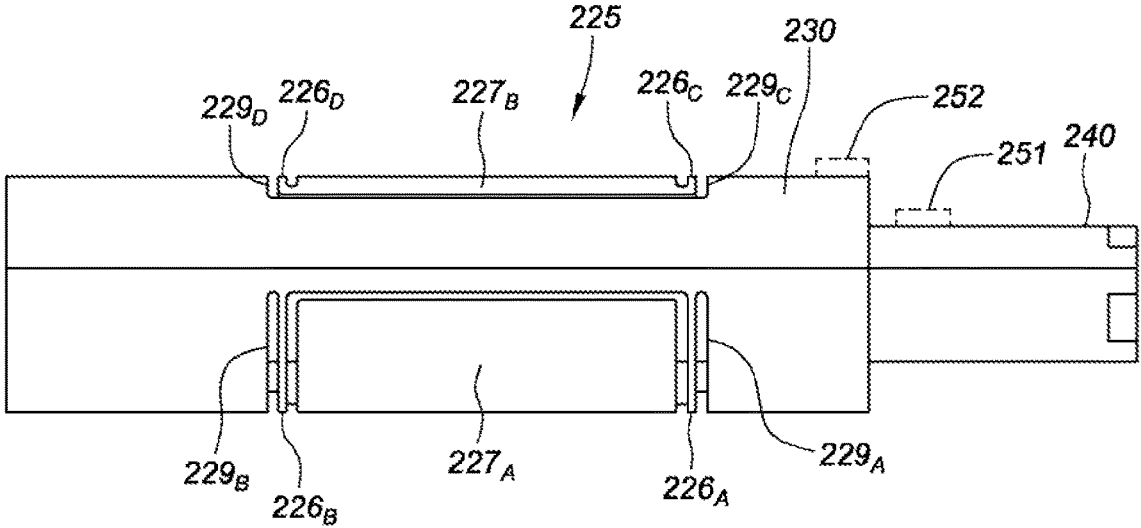
*FIG. 2C*

600

640

625

630

628

$629_A$ $629_B$

626

Section A-A

Section A-A

Section B-B

Table 1

Table 3

CARDIAC CATHETER WITH DEFORMABLE BODY

CROSS-REFERENCE TO RELATED APPLICATION

This application claims the benefit of U.S. provisional application No. 62/455,048, filed 6 Feb. 2017, and U.S. provisional application No. 62/541,805, filed 7 Aug. 2017, which are hereby incorporated by reference as though fully set forth herein.

BACKGROUND a. Field

The instant disclosure relates to various types of medical catheters, in particular catheters for diagnostic testing within, and/or treatment of, a patient's cardiovascular system. In one embodiment, the instant disclosure relates to an ablation catheter for treating cardiac arrhythmias within a cardiac muscle.

b. Background

The human heart routinely experiences electrical currents traversing its myocardial tissue. Just prior to each heart contraction, the heart depolarizes and repolarizes as electrical currents spread through the myocardial tissue. In healthy hearts, the heart will experience an orderly progression of depolarization waves. In unhealthy hearts, such as those experiencing atrial arrhythmia, including for example, ectopic atrial tachycardia, atrial fibrillation, and atrial flutter, the progression of the depolarization wave becomes chaotic.

Catheters are used in a variety of diagnostic and/or therapeutic medical procedures to diagnose and correct conditions such as atrial arrhythmia, including for example, ectopic atrial tachycardia, atrial fibrillation, and atrial flutter. Typically, in such procedures, an intravascular catheter is manipulated through a patient's vasculature to the patient's heart carrying one or more electrodes which may be used for mapping, ablation, diagnosis, or other treatment. Where an ablation therapy is desired to alleviate symptoms including atrial arrhythmia, an ablation catheter imparts ablative energy to myocardial tissue to create a lesion. The lesioned tissue is less capable of conducting electrical signals, thereby disrupting undesirable electrical pathways and limiting or preventing stray electrical signals that lead to arrhythmias. The ablation catheter may utilize ablative energy including, for example, radio frequency (RF), cryoablation, laser, chemical, and high-intensity focused ultrasound. Ablation therapies often require precise positioning of the ablation catheter, as well as precise pressure exertion for optimal ablative-energy transfer into the targeted myocardial tissue. Excess pressure between the ablation catheter tip and the targeted myocardial tissue may result in excessive ablation which may permanently damage the cardiac muscle and/or surrounding nerves. When the contact pressure between the ablation catheter tip and the targeted myocardial tissue is below a target pressure, the efficacy of the ablation therapy may be reduced.

Ablation therapies are often delivered by making a number of individual ablations in a controlled fashion in order to form a lesion line. To improve conformity of the individual ablations along the lesion line, it is desirable to precisely control the position at which the individual ablations are conducted, the ablation period, and the contact pressure between the ablation catheter tip and the targeted tissue. All of these factors affect the conformity of the resulting lesion line. Catheter localization systems, in conjunction with mapping systems, have vastly improved a clinician's ability to precisely position the ablation catheter tip for an ablation. Similarly, ablation controller circuitry has improved the consistency of individual ablation therapy run-times.

The foregoing discussion is intended only to illustrate the present field and should not be taken as a disavowal of claim scope.

BRIEF SUMMARY

The instant disclosure relates to various types of medical catheters. More specifically, the instant disclosure relates to electrophysiology catheters including a deformable body for accurately detecting a force exerted on a distal tip of the catheter.

In one example embodiment of the present disclosure, a force sensing system for a medical catheter is disclosed. The force sensing system includes a deformable body, a permanent magnet, and a magnetic field sensor. The deformable body includes distal and proximal portions, and deflects in response to a force exerted on the distal portion. The permanent magnet is coupled to either the proximal or distal portion of the deformable body. The magnetic field sensor is coupled to the deformable body opposite the permanent magnet. The magnetic field sensor measures a change in magnetic field in proximity to the magnetic field sensor, the change in the magnetic field associated with a change in relative position of the magnetic field sensor and the permanent magnet as the deformable body deflects in response to a force exerted on the distal portion thereof. In more specific embodiments, the force sensing system includes controller circuitry communicatively coupled to the magnetic field sensor, receives a signal from the magnetic field sensor indicative of the magnetic field sensed, and associates the magnetic field with the force exerted on the distal portion of the deformable body.

In another embodiment, an electrophysiology ablation catheter is disclosed. The electrophysiology ablation catheter includes an ablation catheter tip that conducts ablation therapy on tissue, a steerable catheter body, a deformable body, a permanent magnet coupled to the ablation catheter tip, and a magnetic field sensor. The deformable body is coupled to a proximal end of the ablation catheter tip and a distal end of the steerable catheter body. The deformable body includes two or more compliant leaf springs that facilitate deflection of the catheter tip in three spatial dimensions relative to the steerable catheter body. The ablation catheter tip further transfers a force exerted on the catheter tip to the deformable body during an ablation therapy. The magnetic field sensor is coupled to the distal end of the steerable catheter body, and senses a change in a magnetic field in proximity to the sensor which is indicative of a deflection of the deformable body.

The foregoing and other aspects, features, details, utilities, and advantages of the present disclosure will be apparent from reading the following description and claims, and from reviewing the accompanying drawings.

BRIEF DESCRIPTION OF THE DRAWINGS

Various example embodiments may be more completely understood in consideration of the following detailed description in connection with the accompanying drawings.

FIG. 2A is an isometric view of a deformable body, consistent with various aspects of the present disclosure.

FIG. 2B is a front view of the deformable body of FIG. 2A, consistent with various aspects of the present disclosure.

FIG. 2C is a side view of the deformable body of FIG. 2A, consistent with various aspects of the present disclosure.

Figure 1:
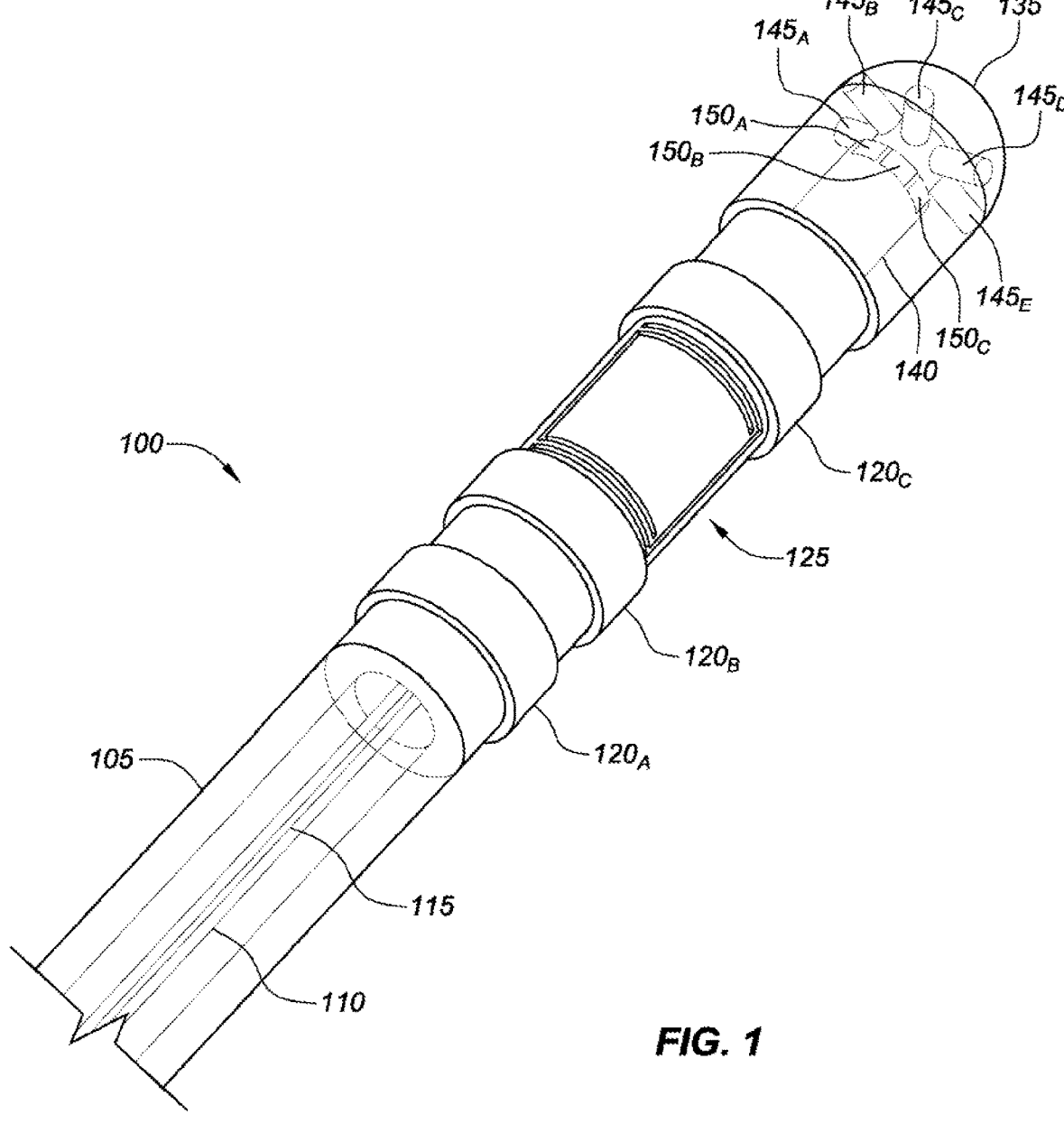
FIG. 1 is an isometric view of a distal portion of an ablation catheter, consistent with various aspects of the present disclosure.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION OF EMBODIMENTS

The instant disclosure relates to electrophysiology catheters. More specifically, the instant disclosure relates to electrophysiology catheters including a deformable body with a tunable trans-axial/axial compliance ratio. In various embodiments, the deformation of the deformable body may be measured to determine a force exerted on a distal tip of a catheter. Details of the various embodiments of the present disclosure are described below with specific reference to the figures.

Referring now to the drawings where like reference numerals are used to identify similar components in the various views, FIG. 1 is an isometric view of a distal portion 100 of a representative ablation catheter, consistent with various aspects of the present disclosure. The distal portion of the ablation catheter includes a distal tip 135 for ablating myocardial tissue using radio frequency emitters 150$_{A-C}$ (also referred to as RF emitters) that emit radiofrequency signals, or other energy, for ablating the tissue in proximity to the distal end of the ablation catheter tip. The RF emitters are controlled by controller circuitry at a proximal end of the catheter shaft 105. The controller circuitry communicates with and transmits the generated radiofrequency signals to the RF emitters via one or more lead wires 115 which are housed within the catheter shaft 105. To prevent blood pooling around the distal tip 135 during ablation therapy, irrigant ports 145$_{A-E}$ emit a saline solution circumferentially around the distal tip 135 in proximity to the tissue being ablated. Fluid lumen 110, housed within the catheter shaft 105, provides a supply of saline solution to the irrigant ports from a reservoir at a proximal end of the catheter shaft 105. In some specific embodiments, the ablation catheter may have a diameter between 7 French ("F") and 8F. The various aspects of the distal tip 135 may be mounted to inner shaft 140.

Electrophysiology (EP) ring electrodes $120_{A-C}$ are swaged or otherwise coupled to an outer diameter of ablation catheter tip 100 at set intervals. The EP ring electrodes can be utilized to map the electrophysiology of a patient's entire cardiac muscle, or a specific chamber such as the left atrium to diagnose cardiac arrhythmias including, for example, atrial flutter and atrial fibrillation. The EP ring electrodes can also determine a source of the erratic electrical signals that cause these arrhythmias. In yet further embodiments, the EP ring electrodes can also be used to initiate cardiac arrhythmias during a procedure, which can further facilitate electrical isolation of unwanted electrical impulses (arrhythmic foci) located in the pulmonary veins. By either destroying the arrhythmic foci, or electrically isolating the foci from the left atrium, for example, the cause of atrial fibrillation can be reduced or eliminated. EP ring electrodes $120_{A-C}$ may be used for other purposes, such as ablation electrodes.

To the extent that arrhythmic foci are located within a tissue ablation zone, the arrhythmic foci are destroyed. To the extent the arrhythmic foci are located in a target pulmonary vein, on the opposite side of an ablation zone from the cardiac muscle, the electrical impulses produced by those foci are blocked or inhibited by the ablation zone.

In a typical ablation therapy for atrial fibrillation, all pulmonary veins are treated. EP ring electrodes $120_{A-C}$ help to expedite diagnosis and treatment of a source of a cardiac arrhythmia, and to confirm a successful ablation therapy by determining the isolation of the arrhythmic foci from the left atrium, for example, or the destruction of the arrhythmic foci entirely.

During an ablation therapy, a distal end 135 of ablation catheter tip 100 contacts ablation targeted myocardial tissue in order to conductively transfer radiofrequency energy from the RF emitters $150_{A-C}$ to the targeted myocardial tissue. It has been discovered that consistent force, during a series of tissue ablations, forms a more uniform and transmural lesion line. Such uniform lesion lines have been found to better isolate the electrical impulses produced by arrhythmic foci, thereby improving the overall efficacy of the ablation therapy. To achieve such consistent force, aspects of the present disclosure utilize a deformable body 125 in the ablation catheter tip. The deformable body deforms in response to forces being exerted upon a distal end 135 of the ablation catheter tip. While various embodiments of the present disclosure are discussed with reference to a magnetic measurement device, the deformation of the deformable body may be measured by one or more measurement devices (e.g., devices employing ultrasonic, magnetic, optical, interferometry, among other technologies). Based on the tuning of the deformable body, the deformation can then be associated with a force exerted on the distal end of the ablation catheter tip (e.g., via a lookup table, formulas, etc.). The measurement device can then output a signal indicative of an external force exerted on the distal portion of the catheter tip. The calculated force can then be displayed to the clinician or otherwise communicated. For example, haptic feedback can be utilized in the catheter handle to indicate proper or insufficient contact force with the targeted myocardial tissue.

As will be discussed in more detail below, deformable body 125 facilitates deflection in three spatial dimensions. More specifically, the deformable body may deform, in response to a force exerted on distal end 135 of ablation catheter tip 100, which results in a bending moment in up to three coordinate axis planes. In one embodiment, the deformable body is further tuned so that the axial compliance of the deformable body, in response to a first force exerted co-axially with the ablation catheter tip, is equal to the trans-axial compliance of the deformable body, in response to the first force exerted trans-axial with the ablation catheter tip. Tuning the deformable body to a trans-axial/axial compliance ratio of 1:1 provides a number of important benefits. For example, during operation, the ablation catheter tip is able to precisely determine the force exerted on the catheter tip regardless of the directionality of the force. Without this linear relationship between the axial and trans-axial compliance of the deformable body, the calculated force error would vary widely depending on the directionality of the force.

In one example embodiment of a distal portion 100 of a representative ablation catheter shown in FIG. 1, a distal end 135 may include an interior cavity within which a permanent magnet may be positioned. Similarly, at a proximal end of the catheter tip (opposite the distal end relative to deformable body 125) a magnetic sensor may be positioned in the interior cavity that extends along a length of the catheter. As the magnetic sensor and permanent magnet are opposite one another, relative to the deformable body 125, a force exerted on the distal end 135 of the ablation catheter tip 100 deforms the deformable body 125 causing a change in the relative positions of the magnetic sensor and permanent magnet. The magnetic sensor (e.g., a Hall effect sensor) senses the change in the magnetic field emitted from the permanent magnet. controller circuitry, communicatively coupled to magnetic sensor, may associate a change in a sensed magnetic field with a deformation of the deformable body 125, and thereby a force exerted on the distal end 135 of the ablation catheter tip 100 (where the deformable characteristics of the deformable body 125 are known). In other embodiments, the placement of the magnetic sensor and permanent magnet may be exchanged.

FIGS. 2A, 2B, and 2C show views of a deformable body 225, consistent with various aspects of the present disclosure. The deformable body 225 comprises an inner shaft 240 and an outer tube 230 which are co-axially coupled to one another, such as via a weld 231 (e.g., a laser weld), at bonding points $227_{A-B}$ of the outer tube. Leaf springs $226_{A-D}$ are cut into the outer tube to form a deformable zone that facilitates deflection in three spatial dimensions. Importantly, dimensional aspects of the leaf springs can be tuned in order to achieve desired compliance ratios related to the displacement of the deformable body in respect to axial and trans-axial forces exerted at a distal end of the inner shaft. In many applications, a compliance ratio of 1:1 may be desirable. Aspects of the present disclosure solve the interdependency problem between axial and trans-axial compliance of a deformable body that has prevented achieving a compliance ratio of 1:1. Accordingly, embodiments consistent with the present disclosure can decrease a trans-axial load compliance of the deformable body without causing a concomitant decrease in the axial load compliance.

Leaf springs $226_{A-D}$ create two separate cross-sections which ensure that a bending moment induced from a trans-axially applied force is not borne by each cross-section under tension/compression alone. Instead, the present embodiment distributes the bending moment across two cross-sections defined by the leaf springs $226_A$, and $226_C$ and the leaf springs $226_B$, and 226D. By distributing the bending moment of the applied force across two cross-sections separated by a distance, the trans-axial/axial compliance ratio of deformable body 225 can be tuned to substantially 1:1.

In various embodiments of deformable body 225, consistent with the present disclosure, outer tube 230 is coupled to a steerable catheter shaft. The movement of bonding points $227_{A-B}$ are substantially independent from the rest of the outer tube due to leaf springs $226_{A-D}$ absorbing the forces exerted on inner shaft 240 and the bonding points (e.g., via weld 231) from the rest of the outer tube. In response to a force exerted upon the inner shaft, the leaf springs $226_{A-D}$ deform. The amount the leaf springs deform is directly correlated to the force exerted on a distal end of the inner shaft. By tuning the dimensions and number of leaf springs in the deformable body, a desired compliance ratio of the deformable body system can be achieved. For example, it can be desirable to have a greater compliance in response to trans-axial forces being exerted on a distal tip of an ablation catheter as the steerable catheter shaft is less capable of exerting forces on myocardial tissue in a trans-axial fashion. Accordingly, by tuning the deformable body to have greater compliance trans-axial to the shaft, a measurement device measuring the deformation (and the associated force related to the deformation) can have increased sensitivity due to the increased trans-axial compliance of the deformable body.

Ablation catheter systems with a deformable body 225 for measuring forces exerted on an ablation tip are susceptible to excess-force events prior and during use of an ablation catheter. These excess-force events can lead to the permanent yielding of components within the deformable body. Such excess-force events can occur, for example, during handling of the ablation catheter, during insertion of the ablation catheter into an introducer sheath, or due to excessively forceful steering of the ablation catheter within the cardiac muscle. When these excess-force events occur, the yielding of one or more portions of the deformable body changes the system dynamics of the deformable body. Importantly, the calibrated correlation between a deformation measurement of the deformable body and an associated force exerted on the ablation catheter tip may no longer be accurate.

To prevent damage to a deformable body 225 due to excess-force events, many embodiments of the present disclosure utilize deformation limiters. The deformation limiters prevent the deformable body from deforming to a yielding point where the calibration between the deformation and the associated force exerted on a catheter tip may no longer be accurate. The embodiments disclosed in FIGS. 2A-C address this problem by utilizing both axial and trans-axial deformation limiters. The axial deformation limiters $229_{A-D}$ limit the deformation of deformable body 225 parallel with a longitudinal axis of the deformable body. In operation, leaf springs $226_{A-D}$ of the deformable body deform in response to axial forces being exerted on the ablation catheter tip. The deformation of the leaf springs absorbs the exerted force, shifting inner shaft 240 axially relative to outer tube 230. Where the axially exerted force exceeds a maximum operating force of the deformable body, the deformed leaf springs come into contact with, and are structurally supported by, the axial deformation limiters $229_{A-D}$ to prevent the leaf springs from yielding under the excessive force.

The trans-axial deformation limiting surface 228 limits the deformation of deformable body 225 in trans-axial directions relative to a longitudinal axis of the deformable body. In operation, leaf springs $226_{A-D}$ of the deformable body deform in response to trans-axial forces being exerted on the ablation catheter tip, shifting inner shaft 240 trans-axially relative to outer tube 230. Where the trans-axially exerted force exceeds a maximum operating force of the deformable body, an inner surface of the outer tube comes into contact with, and structurally supports, the trans-axial deformation limiting surface 228 to prevent the leaf springs from yielding under the excessive force.

To detect the deformation of the deformable body 225, in FIGS. 2A-2C, a permanent magnet may be coupled to inner shaft 240. Accordingly, when the deformable body 225 is assembled within a distal tip of a medical catheter, a force exerted on the distal tip of the catheter is translated through the inner shaft 240 to leaf springs $226_{A-D}$. A magnetic sensor may then be placed on, for example, on outer tube 230 or another portion of the catheter which is not susceptible to movement in response to a force exerted on the catheter tip. As a result of the relative placement of the magnetic sensor relative to the permanent magnet, the magnetic field sensed by the sensor changes in response to a deformation of the deformable body (including the leaf springs $226_{A-D}$). In this way, a force exerted on the catheter tip may be approximated via the output signal of the magnetic sensor. In other embodiments, the placement of the magnetic sensor and permanent magnet may be exchanged.

While various placements of a magnetic sensor and permanent magnet, relative to a deformable body 225, are readily understood in view of the present disclosure, in one example embodiment a magnetic sensor 252 is coupled near a distal end of outer tube 230 while the permanent magnet 251 is coupled in proximity to the magnetic sensor on an inner shaft 240. In such an embodiment, both the permanent magnet and magnetic sensor are positioned distal of the deformable body. In response to a force exerted on the inner shaft 240, the deformable body 225 is deformed changing a relative position between the magnetic sensor 252 and the permanent magnet 251. The magnetic sensor 252 detects the change in magnetic field associated with the relative movement of the permanent magnet 251.

Figure 3C:
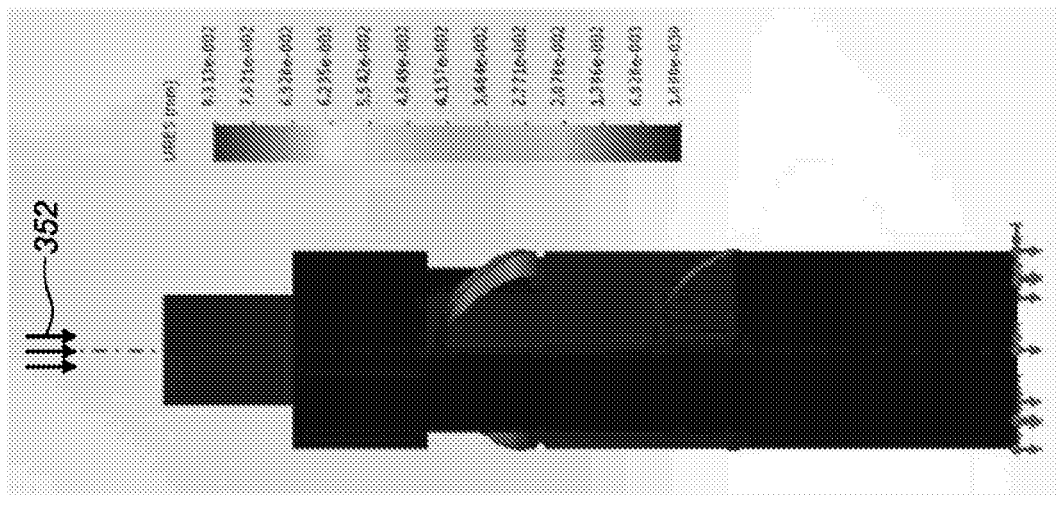
FIGS. 3A-3C are views of a deformable body absorbing forces exerted thereon, consistent with various aspects of the present disclosure.
Figure 3B:
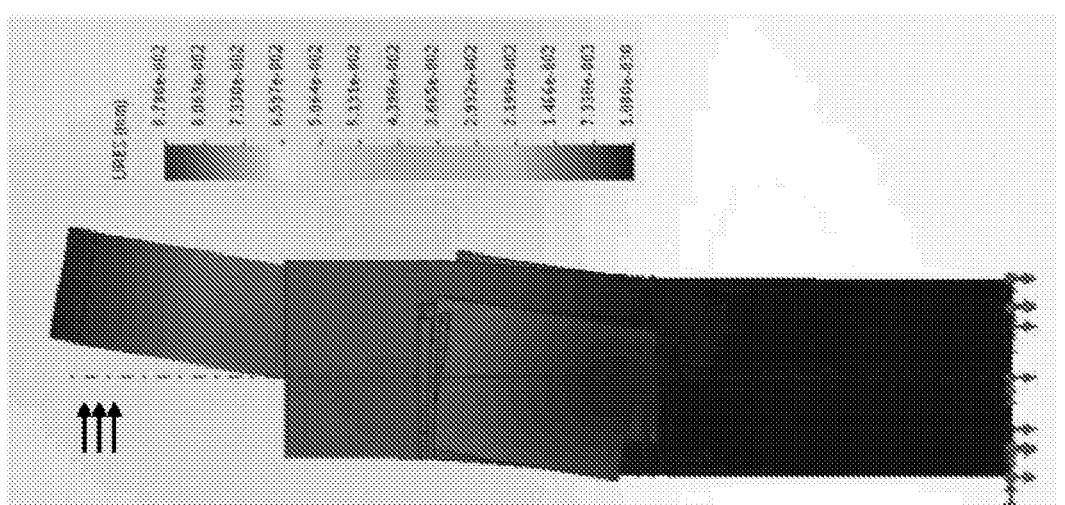
Figure 3A:
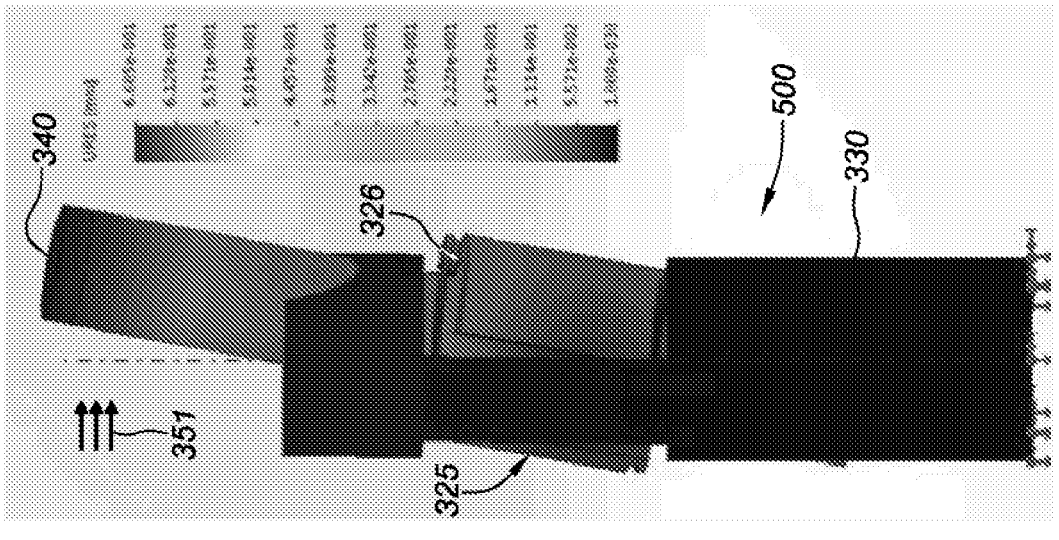

The deformations shown in FIGS. 3A-C are presented in 1:30 scale.

FIG. 3A shows the result of a finite element analysis, where a deformable body 325 of an ablation catheter tip 500 (FIG. 3A is a side view of the deformable body) is responding to a constant trans-axial force 351 of 1 Newton being exerted at a distal end of inner shaft 340, and where the proximal end of outer tube 330 is securely fastened. In response to the constant trans-axial force, leaf springs 326 of the deformable body distort to absorb the trans-axial force. In the present embodiment, the leaf springs have been tuned to deflect approximately 100 micrometers in response to the 1 Newton force on the distal end of the inner shaft (axial or trans-axial).

In some specific embodiments, the deflectable body includes a distal portion, proximal portion, and a deflectable portion therebetween.

FIG. 3B shows the result of a finite element analysis, where a deformable body 325 of an ablation catheter tip 500 is responding to a constant trans-axial force 351 of 1 Newton being exerted at a distal end of inner shaft 340, and where the proximal end of outer tube 330 is securely fastened. FIG. 3A is a front view of the deformable body. In response to the constant trans-axial force, the leaf springs deform to absorb the trans-axial force. As discussed above, the leaf springs have been tuned (by designing the leaf spring cross-section, length, and material) to deflect ~100 micrometers in response to the 1 Newton force on the distal end of the inner shaft (axial or trans-axial). Importantly, aspects of the present disclosure isolate the deformation of the deformable body from the deformable body's material properties that otherwise control the amount of deformation the deformable body experiences in response to the trans-axial force.

FIG. 3C is a side view of the deformable body of FIG. 3A, and shows the results of a finite element analysis where deformable body 325 is responding to a constant axial force 352 of 1 Newton being exerted at a distal end of inner shaft 340. In response to the axial force, leaf springs 326 deform to absorb the axial force. The tuned leaf springs deflect ~100 micrometers in response to the 1 Newton axial force exerted on the distal end of the inner shaft.

Due to the tuning of deformable body 325, the finite element analysis models evidence that regardless of the directionality of a force being exerted on an ablation catheter tip 500, the deformation of the deformable body will be the same for a given exerted force (or resultant force of multiple force vectors). This is particularly useful as it simplifies the correlation between a force exerted on the ablation catheter tip and a measured deformation at the deformable body. Given a tuned deformable body with a trans-axial/axial compliance ratio of 1:1, the deformation of the deformable body associated with a range of forces exerted upon the ablation catheter tip (regardless of the directionality of the force), can be determined and stored in a lookup table. In yet other embodiments, the measured deformation may be input into an algorithm associated with the structural characteristics of the deformable body to determine the force and directionality at the catheter tip. During an ablation therapy procedure, a measurement device can determine the deformation of one or more of the leaf springs relative to a fixed-position and utilize the look-up table to determine the amount of force the ablation catheter tip is experiencing. Without a trans-axial/axial compliance ratio at or near 1:1, the relationship between a force exerted upon the ablation catheter tip and a deformation of the deformable body becomes dependent on the directionality of the exerted force, or a resultant force of a number of force vectors. In one example embodiment, the resultant force is a vector sum of one or more force vectors exerted on the catheter tip.

Tuning a trans-axial/axial compliance ratio of a deformable body to near 1:1 is further desirable as higher compliance ratios can cause clearance related issues with the catheter design. For example, where the trans-axial compliance relative to the axial compliance is too high (e.g., 100:1), the minimum level of axial deflection required for a given measurement system to detect the axial deflection (or have a desired application-specific sensitivity) requires a trans-axial deflection that is the axial compliance multiplied by the compliance ratio of the deformable body. In such a case, the trans-axial deflection can become an unfeasibly large portion of a diameter of the catheter shaft, which prevents the use of the catheter shaft for lead wires, irrigant lumens, etc. Accordingly, aspects of the present disclosure are directed to deformable bodies that facilitate reduced trans-axial/axial compliance ratios.

FIGS. 4A, 4B, 4C, and 4D show a distal portion of an ablation catheter tip assembly 400, consistent with various aspects of the present disclosure. The ablation catheter tip includes a distal end 435 for ablating myocardial tissue using RF emitters therein that emit radiofrequency signals for ablating the tissue in proximity to the distal end of the ablation catheter tip.

To prevent blood pooling around distal end 435 of ablation catheter tip 400 during ablation therapy, irrigant ports 445A-D emit a saline solution circumferentially around the distal end and in proximity to the tissue being ablated. A fluid lumen housed within the catheter shaft provides the saline solution to the irrigant ports.

Electrophysiology (EP) ring electrodes 420$_{A-C}$ are swaged or otherwise connected to an outer diameter of ablation catheter tip 400 at set intervals. The EP ring electrodes facilitate mapping of the electrophysiology of a cardiac muscle, or a specific chamber such as the left atrium to diagnose, for example, a source of the erratic electrical signals responsible for cardiac arrhythmias. As discussed above, the EP ring electrodes can also be used to initiate cardiac arrhythmias.

During an ablation therapy, a distal end 435 of ablation catheter tip 400 contacts ablation targeted myocardial tissue in order to effectively transfer the radiofrequency energy or other energy from the ablation electrodes to the targeted myocardial tissue. As discussed above, it has been discovered that consistent force and/or force above a threshold, during a series of tissue ablations, forms a more uniform lesion line, and thereby improves the overall efficacy of the ablation therapy.

To maintain a minimum force threshold between a distal end 435 of an ablation catheter and tissue being ablated during an ablation therapy, aspects of the present disclosure utilize a deformable body 425 in ablation catheter tip 400. The amount of deformation of the deformable body 425 can be correlated with a cumulative force being exerted upon the distal end 435. The deformation of the deformable body can then be measured by a measurement device and associated with a force exerted on the distal end 435. The calculated force may be displayed to the clinician or otherwise communicated in a way that assists the clinician to maintain a minimum force on the tissue being ablated during both individual ablations and a series of ablations.

In one embodiment, deformable body 425 facilitates deflection in three spatial dimensions (in response to a force exerted on an ablation catheter tip 400). In the present embodiment, the deformable body is tuned with an trans-axial/axial compliance ratio of less than 5:1. With such a low compliance ratio, the ablation catheter tip is able to more precisely determine the force exerted on the catheter tip regardless of the directionality with which the force is exerted upon the ablation catheter tip.

Figure 4A:
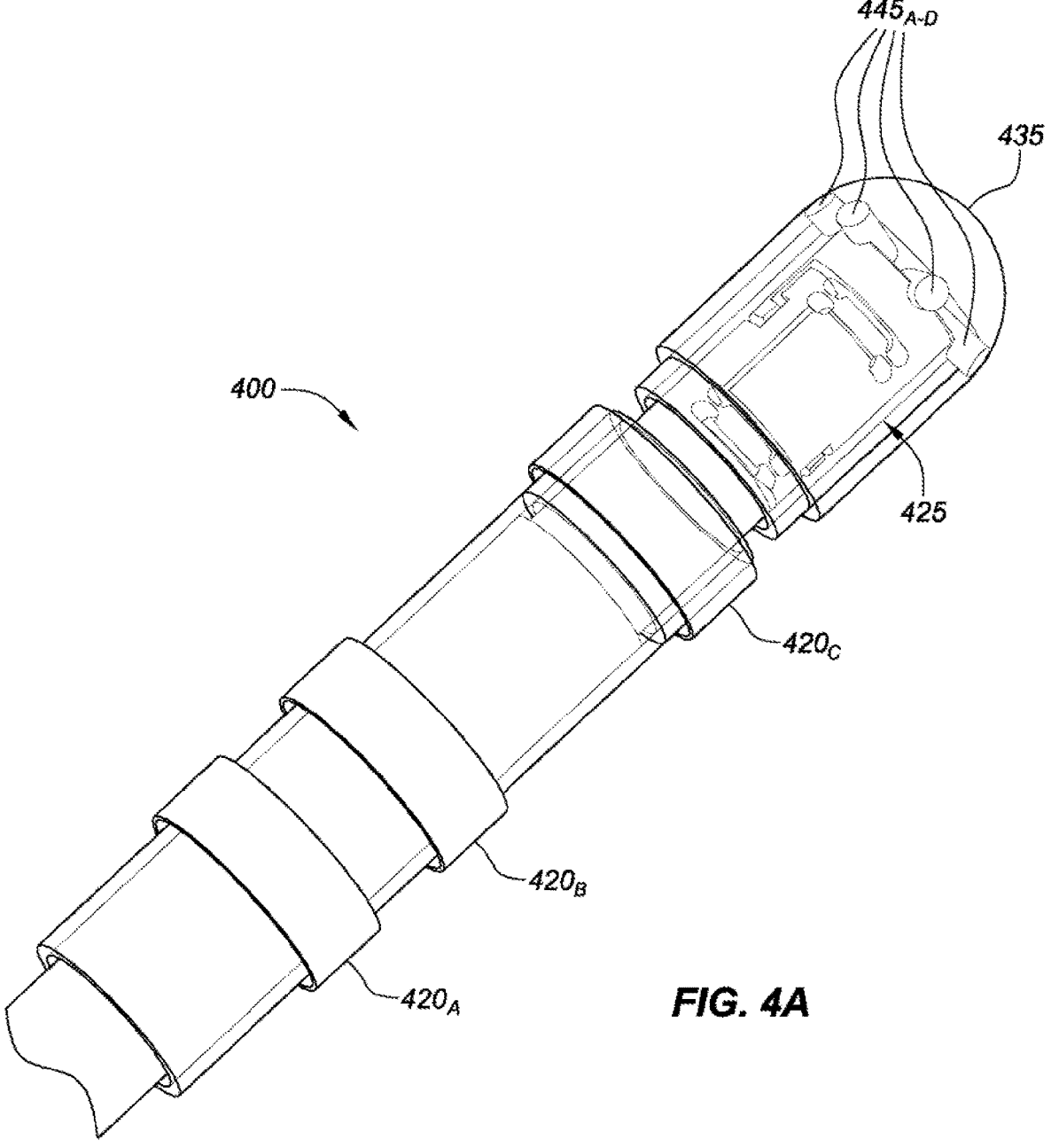
FIG. 4A is an isometric view of a distal portion of an ablation catheter, consistent with various aspects of the present disclosure.
Figure 4B:
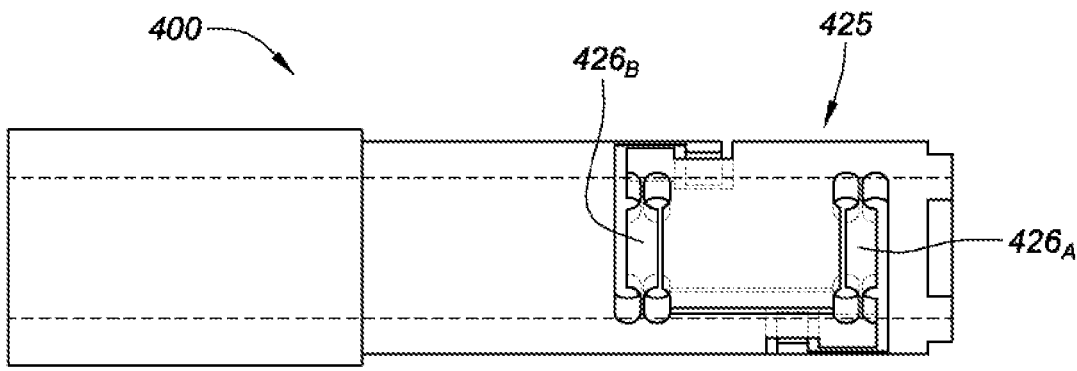
FIG. 4B is a side view of a deformable body of the ablation catheter tip of FIG. 4A, consistent with various aspects of the present disclosure.

Deformable body 425 consists of a single tube with leaf springs 426A-B (as shown in FIG. 4B) cut therein to form a deformation zone that facilitates deflection in three spatial dimensions. The cuts in the tube of the deformable body 425 may be made using various manufacturing techniques (e.g., milling, turning, laser-cutting, electro-erosion, etc.). The leaf springs create two separate cross-sections which divide a bending moment induced from, for example, a trans-axially applied force across each of the cross-sections defined by the leaf springs. By distributing the bending moment of the applied force across two cross-sections separated by a distance, the trans-axial/axial compliance ratio of deformable body 425 can be tuned to substantially 1.

A distal end 435 of an ablation catheter tip 400 and integral deformable body 425, consistent with various aspects of the present disclosure, may comprise a single tube that structurally supports the entirety of the ablation catheter tip and provides the deformable characteristics of the deformable body. The ablation catheter tip can be coupled to a steerable catheter shaft (not shown) to allow for the manipulation of the ablation catheter tip during an ablation therapy within a cardiac muscle. The deformable body 425 allows distal and proximal portions of the ablation catheter tip to be substantially structurally independent from one another, due to leaf springs 426A-B absorbing the forces exerted on distal end 435. In response to a force exerted on the distal tip, the force is translated through the distal end of the ablation catheter tip to the leaf springs where the force is absorbed and the energy is dissipated via deformation of the leaf springs. The amount the leaf springs deform is directly correlated to the force exerted on the distal end. By tuning the dimensions and number of leaf springs in the deformable body, a desired compliance ratio of the deformable body 425 can be achieved. As one example, to achieve an ablation catheter with a trans-axial compliance comparable to the an axial compliance, the compliant leaf springs can have a smaller cross-sectional area or length in a direction transverse to a longitudinal axis of the catheter or separating the leaf spring out along a length of the longitudinal axis. Furthermore, it may be desirable to tune the deformable body so a force exerted on the distal tip of the ablation catheter is linearly related to a deformation of the deformable body. In such embodiments, the complexity of the conversion between a measured deformation to a force exerted on the distal tip can be greatly reduced. In yet other embodiments, it may be desirable to tune the deformable body so that the deformation caused by a force exerted in a direction substantially trans-axial to the catheter body is substantially decreased to limit the amount of clearance required in the catheter body for deformable body deformation. Moreover, in many applications the protective materials/coatings applied to an exterior of the ablation catheter tip can have limited elasticity which may be exceeded by a deformable body that allows for large compliance of the ablation catheter tip.

As discussed above, an ablation catheter tip assembly 400, including a deformable body 425 for measuring forces exerted on an ablation tip, is susceptible to excess-force events, which can lead to permanent yielding of components within the deformable body. When these excess-force events occur, the yielding of one or more portions of the deformable body changes the system dynamics of the deformable body. Importantly, the calibrated correlation between a deformation measurement of the deformable body and an associated force exerted on the ablation catheter tip may no longer be accurate after an excess-force event.

Figure 4C:
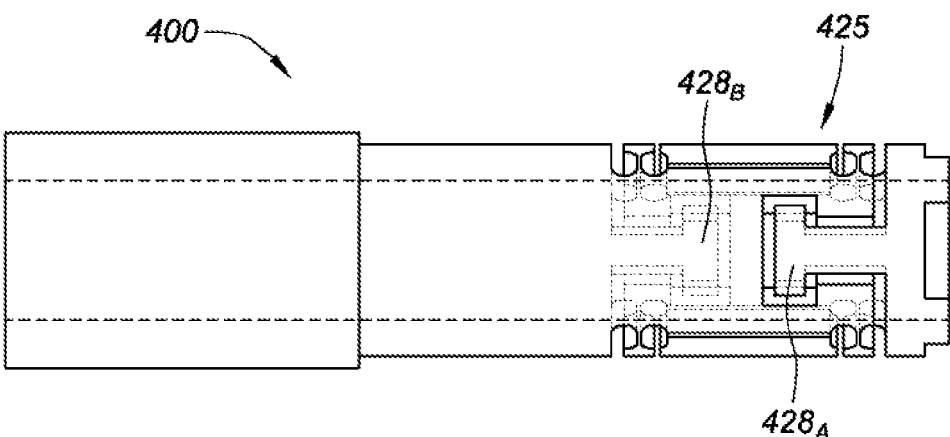
FIG. 4C is a top view of a deformable body of the ablation catheter tip of FIG. 4A, consistent with various aspects of the present disclosure.

To prevent damage to a deformable body 425 due to excess-force events, the present embodiment utilizes deformation limiters 428$_{A-B}$ (as seen in FIG. 4C). The deformation limiters prevent the deformable body from deforming to a yielding point where the calibration between the deformation and the associated force exerted on a catheter tip is no longer accurate. Each of the deformation limiters limits the deformation of the deformable body in both axial and trans-axial directions. In operation, leaf springs 426$_{A-B}$ of the deformable body deform in response to both axial and/or trans-axial forces being exerted on the ablation catheter tip. In response to these exerted forces, the leaf springs deform, off-setting the distal and proximal portions of the ablation catheter tip assembly 400. Where the exerted force exceeds a maximum operating force of the deformable body, one or more of the deformation limiters 428$_{A-B}$ come into contact with a static portion of the deformable body, thereby forming a solid structure across the deformable body and preventing the leaf springs from yielding under the excessive force.

Figure 4D:
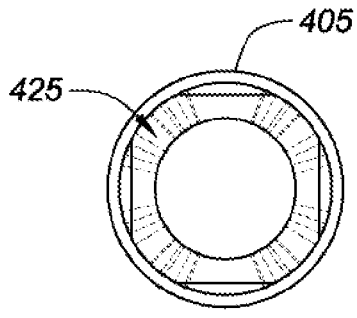
FIG. 4D is a front view of a deformable body of the ablation catheter tip of FIG. 4A, consistent with various aspects of the present disclosure.

FIG. 4D is a front view of a deformable body 425 of the ablation catheter tip of FIG. 4A, consistent with various aspects of the present disclosure. FIG. 4D shows an internal lumen within the deformable body 425, with the invisible lines indicating the various cuts within the deformable body to allow for the desired deformation therein. In the present embodiment, the deformable body 425 has a cross-sectional shape including a circular lumen and a partially rectangular exterior. The deformable body is mounted on to a catheter shaft 405.

Figure 5C:
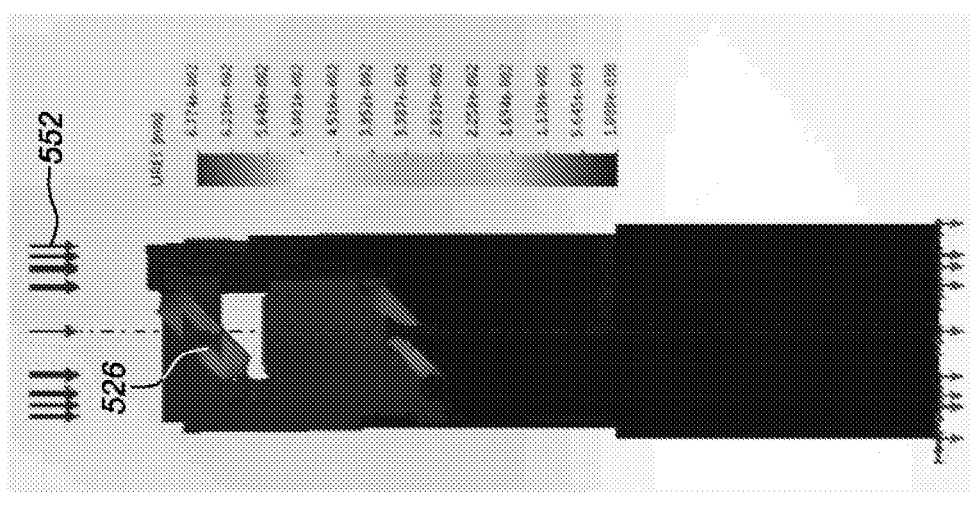
FIGS. 5A-5C are views of a deformable body absorbing forces exerted thereon, consistent with various aspects of the present disclosure.
Figure 5B:
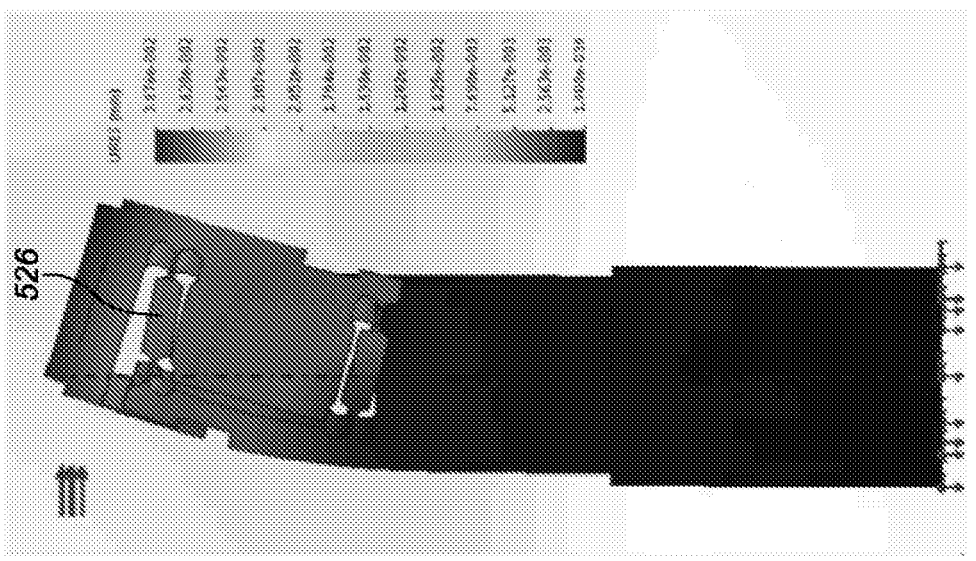
Figure 5A:
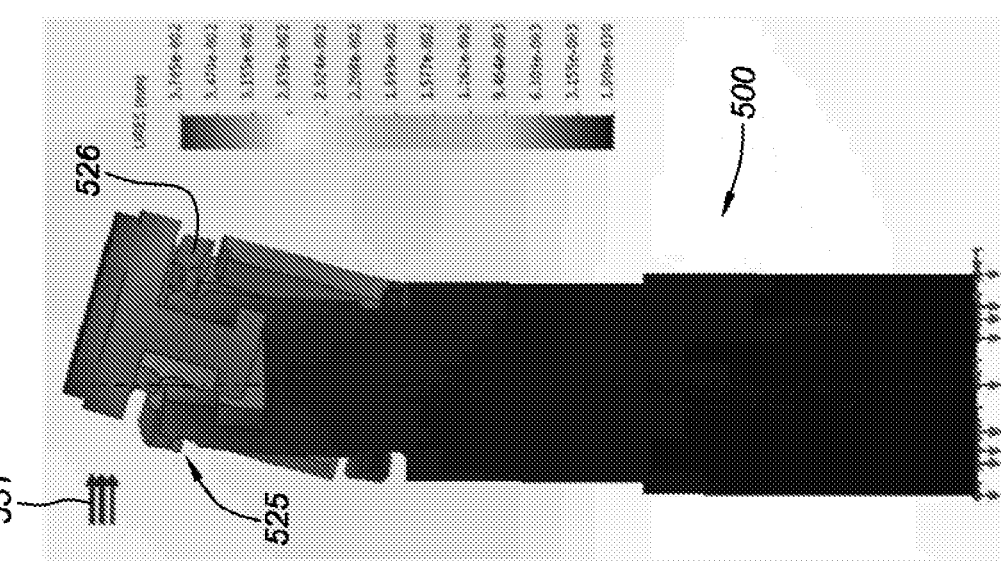

The deformations shown in FIGS. 5A-C are presented in 1:30 scale of a representative embodiment of a deformable body 525.

FIG. 5A is a side view of the deformable body, and shows the result of a finite element analysis where a deformable body 525 is responding to a constant trans-axial force 551 of 1 Newton being exerted at a distal end of ablation catheter tip 500, and where a proximal end of the ablation catheter tip is securely fastened. In response to the constant trans-axial force, leaf springs 526 of the deformable body distort to absorb the trans-axial force. In the present embodiment, the leaf springs have been tuned to deflect approximately 100 micrometers in response to the 1 Newton force on the distal end of the inner shaft.

FIG. 5B is a front view of the deformable body of FIG. 5A, and similar to FIG. 5A shows the results of a finite element analysis where the deformable body is responding to a constant trans-axial force of 1 Newton being exerted at a distal end of inner shaft, and where the proximal end of outer tube is securely fastened. In response to the constant trans-axial force, the leaf springs deform to absorb the trans-axial force. As discussed above, the leaf springs have been tuned (by designing the leaf spring cross-section, length, and material) to deflect approximately 100 micrometers in response to the 1 Newton force on the distal end of the inner shaft.

FIG. 5C is a side view of the deformable body of FIG. 5A, and shows the result of a finite element analysis where the deformable body is responding to a constant axial force 552 of 1 Newton being exerted at a distal end of the inner shaft, and where the proximal end of the outer tube is securely fastened. In response to the constant axial force, the leaf springs 526 deform to absorb the axial force. The tuned leaf springs deflect approximately 100 micrometers in response to the 1 Newton force on the distal end of the inner shaft.

Due at least in part to the tuning of deformable body 525, the finite element analysis models evidence that regardless of the directionality of a force being exerted on an ablation catheter tip, the deformation of the deformable body will be the same for a given exerted force (or resultant force of multiple force vectors). This is particularly useful as this simplifies the correlation between a force exerted on the ablation catheter tip and a measured deformation at the deformable body. Given a tuned deformable body with a trans-axial/axial compliance ratio of 1:1, for example, the deformation of the deformable body associated with a range of forces exerted upon ablation catheter tip 500 can be determined and stored in a lookup table. During an ablation therapy procedure, a measurement device can determine the deformation of one or more of the leaf springs relative to a fixed-position and utilize the look-up table to determine the amount of force the ablation catheter tip is experiencing.

Figures 6A, 6B, 6C:
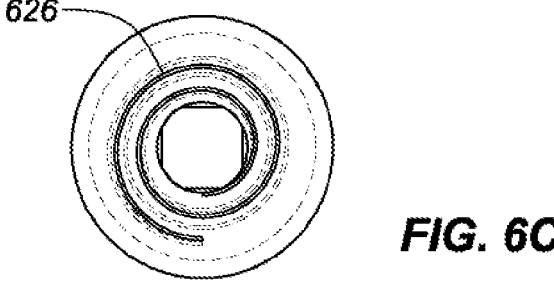
FIG. 6A is an isometric view of a deformable body, consistent with various aspects of the present disclosure.
FIG. 6B is a side view of the deformable body of FIG. 6A, consistent with various aspects of the present disclosure.
FIG. 6C is a front view of the deformable body of FIG. 6A, consistent with various aspects of the present disclosure.

FIGS. 6A, 6B, and 6C show views of a portion of an ablation catheter tip 600 including a deformable body 625, consistent with various aspects of the present disclosure. The deformable body consists of an inner shaft 640 (including proximal portion 628) and an outer tube 630 which are co-axially coupled to one another via a flat spring 626 that is circularly wound about the inner shaft. Importantly, dimensional aspects of the flat spring can be tuned in order to achieve desired compliance ratios related to the displacement of the deformable body in respect to axial and trans-axial forces exerted at a distal end of the inner shaft. In many applications, as discussed above, a compliance ratio approaching 1 may be desirable. In one example embodiment, where the trans-axial deflection of the deformable body 625 is greater than an axial deflection, a width of the flat spring may be extended, and/or a length of the flat spring minimized, and/or a thickness of the flat spring increased, in order to tune the compliance ratio between the axial and trans-axial compliance ratio to around 1:1 (or some other desirable compliance ratio or performance characteristic).

In various embodiments of deformable body 625, consistent with the present disclosure, outer tube 630 is coupled to a steerable catheter shaft. The movements of the outer tube relative to inner shaft 640 are substantially independent due to flat spring 626 absorbing the forces exerted on the inner shaft by deforming. The amount the flat springs deform is directly correlated to the force exerted on a distal end of the inner shaft 640. By tuning the cross-sectional dimension and the number of windings of the flat spring encircling the inner shaft, a desired compliance ratio of the deformable body can be achieved.

In other embodiments consistent with the present disclosure, the deformable body 625 of FIGS. 6A-C may include one or more flat springs 626 which may be wound co-axial with one another and/or offset from one another along a longitudinal axis of the catheter shaft. In further embodiments, it may be desirable to have two or more flat springs 626 wound around the inner shaft 640 in opposite directions to counteract any change in spring rates associated with the flat springs winding or un-winding in response to a rotational force along the longitudinal axis of the inner shaft 640.

To limit the deformation of flat spring 626 of deformable body 625 along a longitudinal axis of the catheter, hard stops 629A-B may be positioned on either side of flat spring 626. In some embodiments, a single hard stop may be positioned near a proximal end of flat spring 626. The one or more hard stops may be positioned at such a distance from the un-deformed state of the flat spring as to prevent the spring from reaching plastic deformation in response exerted thereon.

Figures 7A, 7B, 7C:
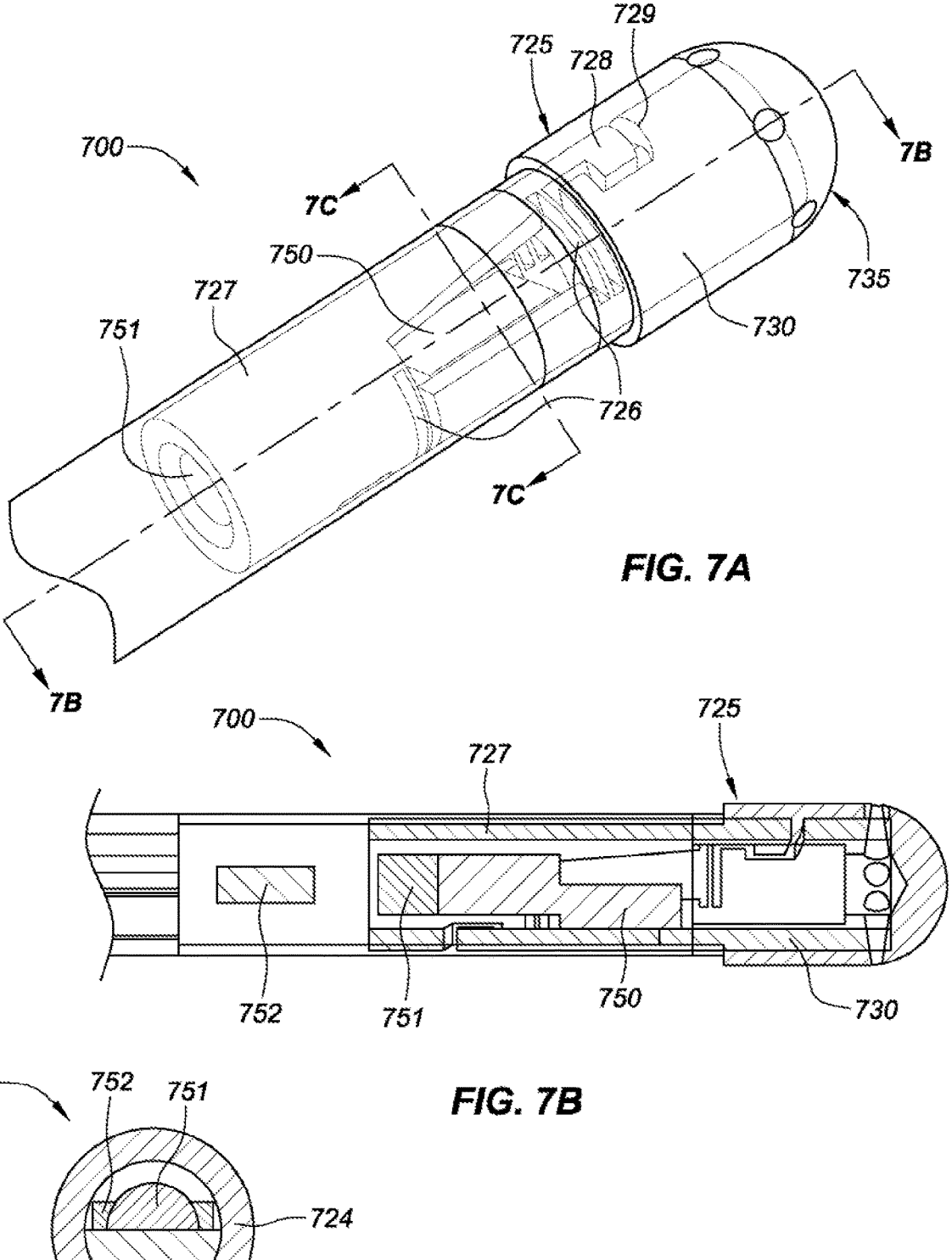
FIG. 7A is an isometric view of an ablation catheter tip including a deformable body, consistent with various aspects of the present disclosure.
FIG. 7B is a cross-sectional side view of the ablation catheter tip and deformable body of FIG. 7A, consistent with various aspects of the present disclosure.
FIG. 7C is a cross-sectional front view of the ablation catheter tip and deformable body of FIG. 7A, consistent with various aspects of the present disclosure.

FIG. 7A is an isometric view of an ablation catheter tip 700 including a deformable body 725 for determining a force applied to a distal tip 735 of the catheter. A distal portion 730 of the deformable body 725 is coupled to the distal tip 735. A proximal portion 727 of the deformable body 725 is coupled to a catheter shaft. When the distal tip is contacted (e.g., by myocardial tissue within a cardiac muscle), the spatial positioning of the distal portion 730 may be displaced relative to the proximal portion 727 via one or more leaf springs 726 of the deformable body which are coupled there between. In response to the distal portion 730 of the deformable body receiving a force from the distal tip 735, the one or more leaf springs 726 may deform thereby changing the spatial relationship between the proximal and distal portions of the deformable body. The distal portion 730 is further coupled to a beam 750 that extends proximally along a longitudinal axis of the catheter. The proximal portion of the beam 750 facilitates a permanent magnet 751 that moves in kind with the distal portion 730 of the deformable body 725 in response to a force being exerted on the distal tip. A magnetic sensor 752 (e.g., a digital Hall probe), as shown in FIG. 7B, is coupled to a proximal portion 727 of the deformable body 725, and is isolated from the deformation of the deformable body in response to a force exerted on the distal tip 735. Accordingly, the magnetic sensor 752 may track a change of position of the permanent magnet 751, relative to the static position of the magnetic sensor.

To limit the deformation of the leaf springs 726 and the relative spatial movement of distal and proximal portions (730 and 727, respectively,) of deformable body 725, the deformable body may further include deformation limiters.

For example, one or more trans-axial deformation limiters 728 may be coupled to the proximal portion 727 of the deformable body 725. In response to a force exerted on the distal tip 735 that may induce a bending and/or rotational force beyond the yield strength of the leaf spring 726 material (or beyond a sensing range of the magnetic sensor 752), the trans-axial deformation limiter 728 contacts a surface of the distal portion 730 to form a solid structure between the proximal and distal portions of the deformable body 725. This solid structure limits further deformation, and prevents damage to the leaf springs 726. Similarly, the trans-axial deformation limiting feature 728 may further be used in association with an axial deformation limiting feature 729 on the distal portion 730 to prevent over-contraction of the distal portion 730 in response to an axial force being exerted on the distal tip 735. Specifically, where the axial force exerted may exceed a yield strength of the leaf springs 726, the axial deformation limiting feature 729 is extended into contact with the trans-axial deformation limiting feature 728—thereby forming a solid structure that will not facilitate deformation of the deformable body in an axial direction. Such a scheme may also be used to limit the range of the deformable body 725 to that which may be measured by the magnetic sensor 752.

It is to be understood that the material characteristics and the dimensions of leaf springs 726 and the length of beam 750 may be calibrated to optimize the movement of the beam in response to an expected range of forces exerted on a distal tip 735 for a given medical application. Furthermore, the leaf springs and the beam may further be calibrated to suit the specifications of a magnetic sensor 752. For example, where the magnetic sensor has a resolution for detecting movement of a specific permanent magnet of 0.1 millimeters, the material characteristics and dimensional characteristics for the leaf springs 726 may be selected for a given range of application forces (e.g., forces exerted on the distal tip 735 between 0-10 grams) that allows total use of the sensor resolution range. Similarly, the length of the beam 750 may be selected in accordance with the off-axis sensor resolution and the angular off-axis displacement of the deformable body in response to a given range of trans-axial force application on the distal tip 735.

FIG. 7B is a cross-sectional side view of the ablation catheter tip 700 including deformable body 725 of FIG. 7A. As shown in FIG. 7B, when an axial force is exerted upon the ablation catheter tip 700, distal portion 730 of the deformable body 725 and beam 750 (coupled thereto) are extended into closer proximity with proximal portion 727 of the deformable body and a magnetic sensor 752 coupled to the proximal portion. As a result, a permanent magnet 751 coupled to a proximal end of the beam 750 is extended into closer proximity with the magnetic sensor 752. The magnetic sensor 752, in response to the change in spatial relationship with the permanent magnet 751 outputs an electrical signal that fluctuates in one or more measurable characteristics. The electrical characteristic fluctuation of the output signal is indicative of a force exerted on the distal tip of the catheter. Where the magnetic sensor is a Hall effect sensor, the sensor varies its output voltage in response to a magnetic field. With a known magnetic field (e.g., known permanent magnet), a distance between the Hall plate and the permanent magnet may be determined. The output of the Hall effect sensor may be transmitted through a length of the catheter shaft to signal processing circuitry including a linear circuit to receive and process the sensor's output signal. The linear circuit may provide a constant driving current to the sensor, as well as amplify the received output signal. As discussed in more detail below, the signal processing circuitry may further cancel an offset voltage of the sensor, as well as other advanced corrections of the sensor's characteristics (e.g., temperature coefficient corrections, and correcting for the portion of the output signal associated with Earth's magnetic field).

Where an ablation catheter tip 700 experiences a trans-axial force, deformable body 725 deforms. The deformation of the deformable body misaligns the otherwise co-axial arrangement of proximal and distal portions, 727 and 730, respectively. As beam 750 is coupled to the distal portion, the axial alignment of magnetic sensor 752 and permanent magnet 751 is lost-thereby extending the distance between the magnetic sensor and permanent magnet, and reducing the sensed strength of the permanent magnet's magnetic field at the magnetic sensor. Specifically, the magnetic field strength varies inversely with the third power of distance, or in other words—the strength of the magnetic field for a given permanent magnet is equal to 1/distance^3. As a result, even a small change in the distance between a magnetic field source and a magnetic sensor will greatly reduce the sensed magnetic field, which facilitates an advantageous resolution ratio for the sensor (i.e., a small distance change is sensed as a large change in sensed magnetic field).

FIG. 7C is a cross-sectional front view of ablation catheter tip 700 of FIG. 7A. This cross-sectional front view shows the axial arrangement of a permanent magnet 751 coupled to a beam 750, relative to a magnetic sensor 752. Importantly, as discussed above in relation to trans-axial forces, the beam may extend the permanent magnet 751 away from a longitudinal axis of the catheter. An outer tube with a large inner diameter facilitates radial motion of the permanent magnet 751. Depending on the resolution capability of the magnetic sensor, a diameter of an inner lumen of catheter shaft 724 and a length of the beam 750 may be selected to match the sensing resolution to a desired trans-axial force range. Further, an inner diameter of the catheter shaft 724 may be used as a deformation limiter, to prevent leaf springs 726 from yielding and/or to physically limit a range of sensor measurement. In such an embodiment, the magnet 751 and/or the beam 750 will contact the inner diameter of the catheter shaft 724 to form a solid structure, absorbing at least a portion of the force exerted on the deformable body 725, and preventing the leaf springs 726 from yielding.

Figure 8:
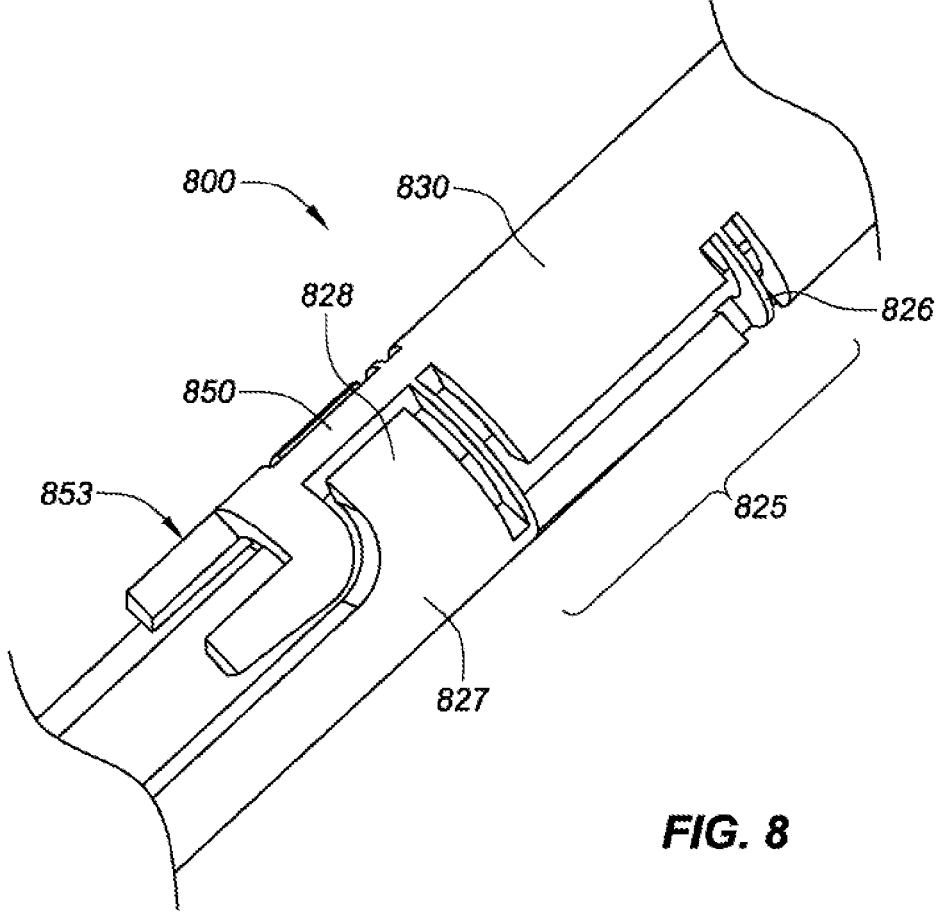
FIG. 8 is an isometric view of a portion of an ablation catheter tip, consistent with various aspects of the present disclosure.

FIG. 8 is an isometric view of a portion of an ablation catheter tip 800 including a deformable body 825. A distal portion 830 of the deformable body 825 is coupled to a tip that may be subject to external forces. In response to external force on the tip, the force is transmitted through the distal portion 830 and exerted on the deformable body 825, including leaf springs 826, as a torque. In response to the torque, the leaf springs 826 deform to facilitate one or both of: spatial repositioning between the distal portion 830 and a proximal portion 827 of the deformable body 825, and axial misalignment of the distal and proximal portions. As a result of the spatial repositioning and/or the axial misalignment between the distal and proximal portions, a magnetic sensor mounted to the proximal portion 827 will detect the relative change in position with a permanent magnet mounted to holder 853 at the proximal end of beam 850.

In other embodiments, the deformable body arrangement may be essentially mirrored to the embodiment shown in FIG. 8. That is, the beam may be coupled to a proximal portion of the deformable body, and a magnetic sensor/permanent magnet in the holder 853 may remain static in response to a force exerted on the catheter tip. In such an embodiment, the permanent magnet/magnetic sensor may be mounted directly to the distal portion of the deformable body. Regardless of the magnetic sensor position (on either the beam or the distal portion), the magnetic sensor will detect a change in magnetic field strength due to the varying relative position of the permanent magnet, in response to an external force applied to the catheter tip deforming the deformable body. The change in the sensed magnetic field by the magnetic sensor is indicative of both the relative distance between the magnetic sensor and permanent magnet, and the external force applied to the catheter tip.

Similar to the embodiment of FIG. 7A, FIG. 8 includes deformation limiting feature 828. Specifically, where the axial/trans-axial force exerted on a distal tip of the catheter exceeds a yield strength of the deformable body 825, the deformation limiting feature 828 is extended into contact with beam 850 and/or one of springs 826—thereby forming a solid structure that will not further deform.

Figure 9A:
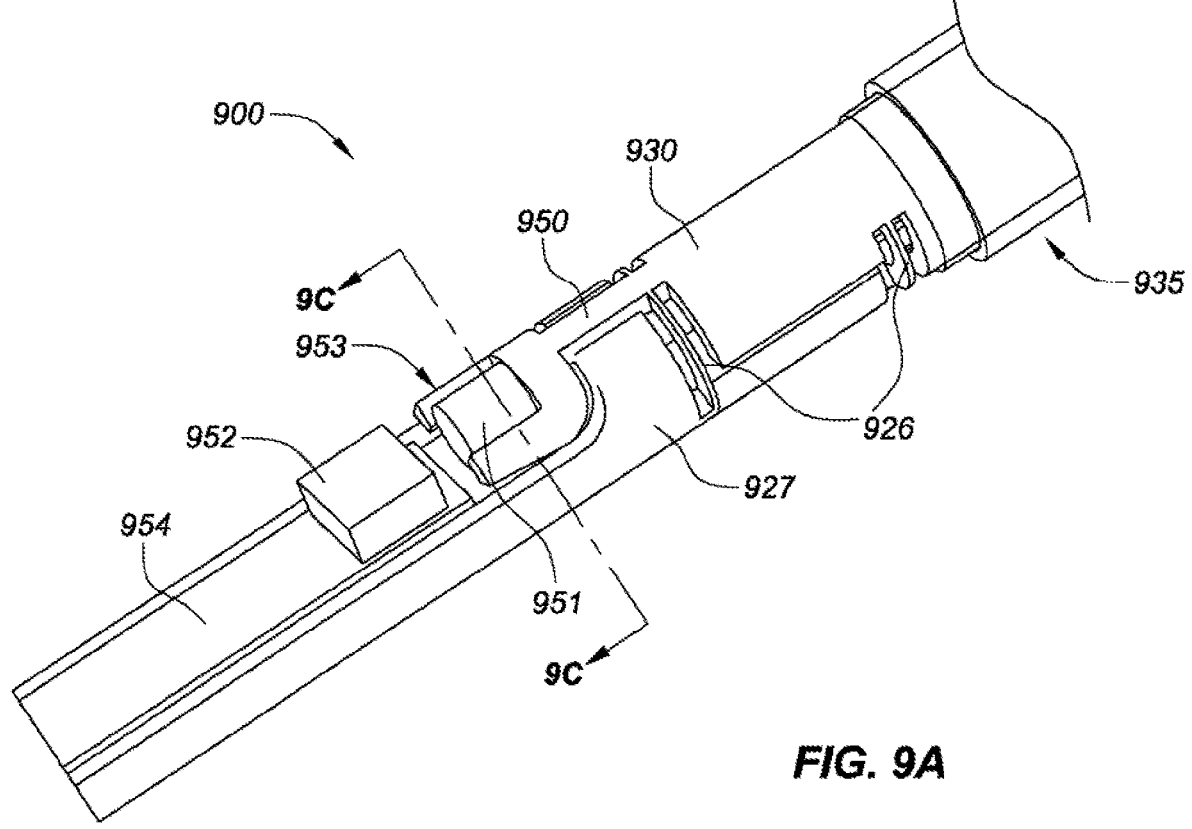
FIG. 9A is an isometric view of a force sensor integrated into a catheter tip assembly, consistent with various aspects of the present disclosure.

FIG. 9A is an isometric view of a force sensor 900 integrated into an ablation catheter tip. In the present embodiment, the force sensor components have been moved away from a central axis of the catheter shaft to facilitate wiring, irrigant lumens, or a central lumen to extend through a length of the catheter shaft. A deformable body includes proximal portion 927, distal portion 930, and leaf springs 926. The distal portion 930 is coupled to a distal tip 935 of the ablation catheter, and in response to a force exerted on the distal tip transmits the exerted force to the leaf springs 926. In response to the exerted force, the leaf springs 926 deform to absorb the exerted force which temporarily modifies a spatial relationship between the distal portion 930 and the proximal portion 927. To measure this change in the spatial relationship, a magnetic sensor 952 (also referred to as a magnetic field sensor) is utilized. The magnetic sensor is communicatively coupled to a flexible electrical circuit 954 that extends a length of the catheter shaft-thereby facilitating communication of the resulting magnetic sensor signal with signal processing and/or controller circuitry. Both the magnetic sensor 952 and the flexible electrical circuit 954 are coupled to the proximal portion 927, which remains static in response to an exerted force on the distal tip 935. However, a permanent magnet 951 (or a piece of ferrite metal, or an electro-magnet), which is paired with the magnetic sensor 952, is coupled to the dynamic distal portion 930 via beam 950 and magnet holder 953. In some embodiments, the beam 950 may function as a cantilevered beam. When a force is exerted on the distal tip 935, the leaf springs 926 facilitate relative motion of the distal and proximal portions of the deformable body. Accordingly, the spatial relationship between the magnetic sensor 952 and the permanent magnet 951 is dynamic.

Where a force exerted is axial to a catheter shaft, the distance between a magnetic sensor 952 and permanent magnet 951 is decreased; thereby increasing the strength of the magnetic field sensed by the magnetic sensor. The magnetic sensor outputs a signal indicative of the magnetic field sensed and controller circuitry interprets that signal to first determine a relative distance between the magnetic sensor and the permanent magnet given the known magnetic properties of the permanent magnet. Second, the controller circuitry associates the distance between the magnetic sensor and the permanent magnet with a force (and vector of the force) exerted on the catheter tip. The force determination may be based on an algorithm (e.g., associating the known material characteristics and dimensions of the leaf springs 926), or some form of calibration (e.g., implementing a best-fit curve between look-up table data points).

Figures 9B, 9C, 9D:
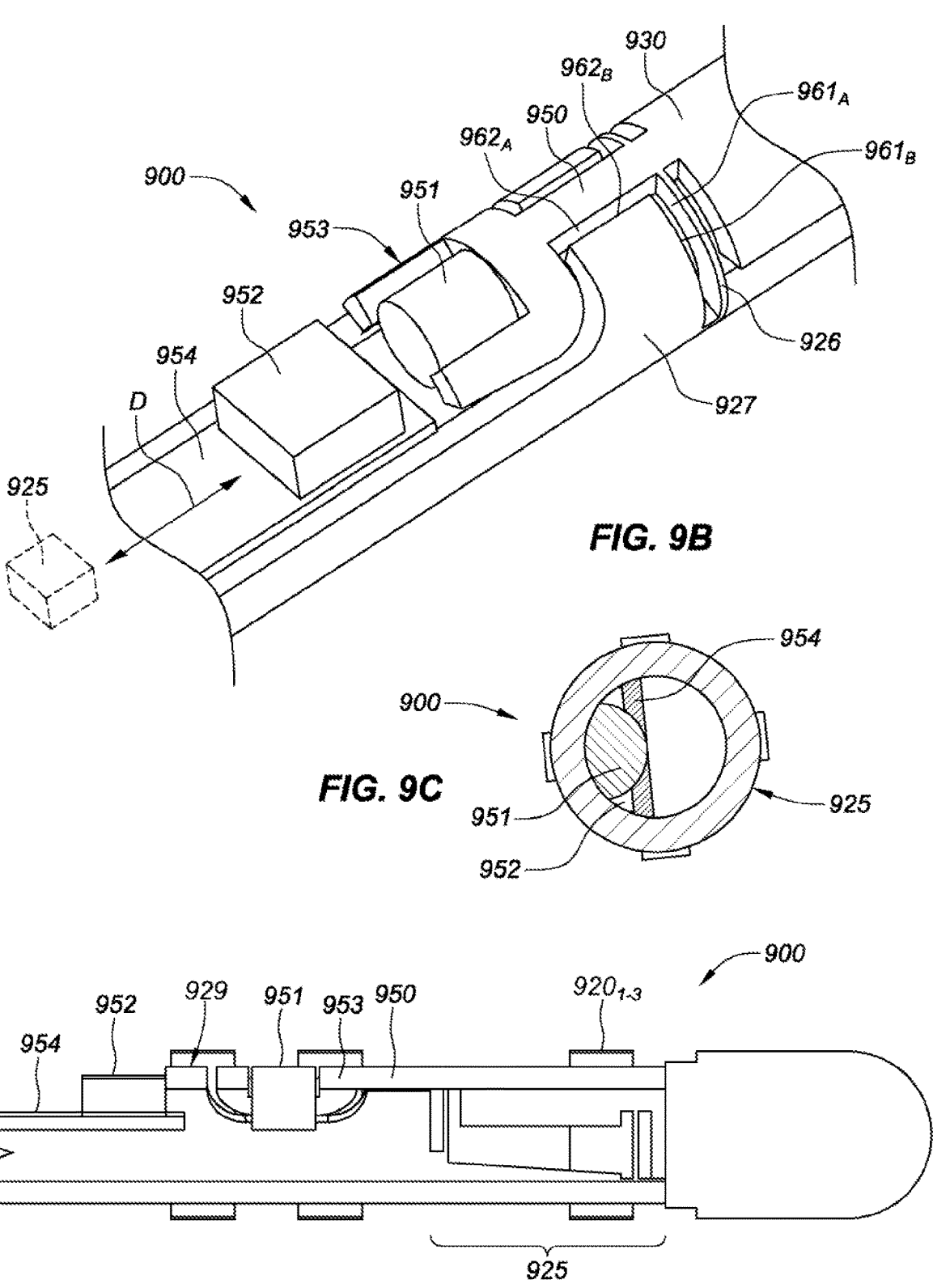
FIG. 9B is a close-up isometric view of the force sensor of FIG. 9A, consistent with various aspects of the present disclosure.
FIG. 9C is a cross-sectional front view of the force sensor of FIG. 9A, consistent with various aspects of the present disclosure.
FIG. 9D is a side view of another ablation catheter tip and deformable body, consistent with various aspects of the present disclosure.

FIG. 9B is a close-up, isometric view of the force sensor 900 of FIG. 9A. As shown in FIG. 9B, leaf springs 926 couple distal portion 930 and proximal portion 927 of the deformable body to one another. To prevent damage to the leaf springs 926 associated with exceeding a yield strength of the leaf spring's material, deformation limiters may be utilized. Moreover, by limiting the motion of the deformable body, unintentional contact between the magnetic sensor 952 and the permanent magnet 951 (and/or magnet holder 953) may be prevented. Such unintentional contact between the magnetic sensor and the permanent magnet may cause damage to the electrical contacts between the magnetic sensor and flexible electronic circuit 954, and/or disrupt the static placement of the magnetic sensor 952 on the proximal portion 927 of the deformable body. Axial deformation limiting surfaces $961_{A-B}$, in response to an axial force exceeding a yield strength of the leaf springs 926 will contact one another forming a solid structure that prevents further axial deformation of the deformable body. Similarly, trans-axial deformation limiting surfaces $962_{A-B}$, in response to a trans-axial force on the catheter tip exceeding a yield strength of the leaf springs 926 will contact one another to form a solid structure that prevents further trans-axial deformation of the deformable body.

In some embodiments of the force sensor 900 as shown in FIG. 9B, a secondary magnetic sensor 925 may be added at a location proximal to a first magnetic sensor 952, and outside of a magnetic field of permanent magnet 951. The first magnetic sensor 952 is placed at a distance D from the secondary magnetic sensor 925, but are planar relative to one another to facilitate the sensors being subjected to the same magnitude of the Earth's magnetic field at a time, T. In some embodiments, various objects within an electrophysiology lab may induce additional magnetic fields of various magnitudes and vectors (e.g., tertiary magnetic fields)—the planar orientation of the magnetic sensors facilitate sensing and filtering of such fields from the sensed field associated with a magnetic field of the permanent magnet 951. The secondary magnetic sensor 925 only detects the Earth's magnetic field (and any other tertiary magnetic fields). The first magnetic sensor 952, however, detects both the Earth's magnetic field, any tertiary fields, and a field emitted by the permanent magnet 951. Back-end processing circuitry may receive both the signals from the first and secondary magnetic sensors, and filter out the Earth's magnetic field signal (and any other tertiary magnetic fields) from the first magnetic sensor's signal to improve a signal-to-noise ratio-thereby facilitating improved force sensor measurement accuracy and resolution.

FIG. 9C is a cross-sectional, front view of the force sensor 900 of FIG. 9A. In the present embodiment, the force sensor components (including magnetic sensor 952, permanent magnet 951, and beam 950) have been moved away from a central axis of the catheter shaft to free up cross-sectional space within a central lumen of the catheter shaft. Moreover, deformable body 925 components (including proximal portion 927, distal portion 930, and leaf springs 926) are integrated into an outer tube. Accordingly, the ablation catheter may include an integral force sensor 900 while a central lumen within the catheter shaft facilitates wiring, irrigant lumen(s), etc.

FIG. 9D is a side view of another ablation catheter tip 900 with magnetic field sensing, consistent with various aspects of the present disclosure. As shown in FIG. 9D, the force sensor components (including the deformable body 925) have been moved away from a central axis of the catheter shaft to facilitate wiring, irrigant lumens, or a central lumen to extend through a length of the catheter shaft. The deformable body 925, in response to a force exerted on the ablation catheter tip 900, deforms to absorb the exerted force on the catheter tip. A beam 950 that extends over the deformable body 925 has a holder 953 at a proximal end that is coupled to a permanent magnet 951. When the deformable body 925 deforms in response to a force exerted on the catheter tip, a spatial relationship between the permanent magnet 951 and a magnetic sensor 952 (such as a digital Hall probe) is temporarily modified. To measure this change in the spatial relationship, the magnetic sensor 952 is communicatively coupled to a flexible electrical circuit 954 that extends a length of the catheter shaft-thereby facilitating communication of the resulting magnetic sensor signal with signal processing and/or controller circuitry. Both the magnetic sensor 952 and the flexible electrical circuit 954 are coupled to a proximal portion of the catheter tip (and proximal the deformable body 925), which remains static in response to the exerted force on the distal tip.

Where a force exerted is axial to a catheter shaft, the distance between a magnetic sensor 952 and permanent magnet 951 is decreased; thereby increasing the strength of the magnetic field sensed by the magnetic sensor. Where a force exerted is trans-axial to a catheter shaft, the distance between a magnetic sensor 952 and permanent magnet 951 is increased, thereby reducing the strength of the magnetic field sensed by the magnetic sensor. The magnetic sensor 952 outputs a signal indicative of the magnetic field sensed and controller circuitry interprets that signal to first determine a relative distance between the magnetic sensor and the permanent magnet given the known magnetic properties of the permanent magnet. Second, the controller circuitry associates the distance between the magnetic sensor and the permanent magnet with a force (and, in some cases, vector of the force) exerted on the catheter tip. The force determination may be based on an algorithm (e.g., associating the known material characteristics and dimensions/dynamics of the deformable body 925), or some form of calibration (e.g., implementing a best-fit curve between look-up table data points).

In FIG. 9D, as a known, at-rest position of a magnetic sensor 952 relative to a permanent magnet 951 may be critical to accurate force sensing, a hard stop 929 precisely locates the flexible electronic circuit 954 (and magnetic sensor 952) relative to the permanent magnet 951. The hard stop 929 may also be used to limit the stroke of the deformable body 925, beam 950, and holder 953 in an axial direction.

In accordance with the present disclosure, it has also been discovered that positioning electrophysiology ring electrodes 9201-3 in proximity to the interface between the permanent magnet 951 and magnetic sensor 952 may help to shield the interface from undesirable electro-magnetic interface that may distort the signal received by the magnetic sensor 952.

Figure 10:
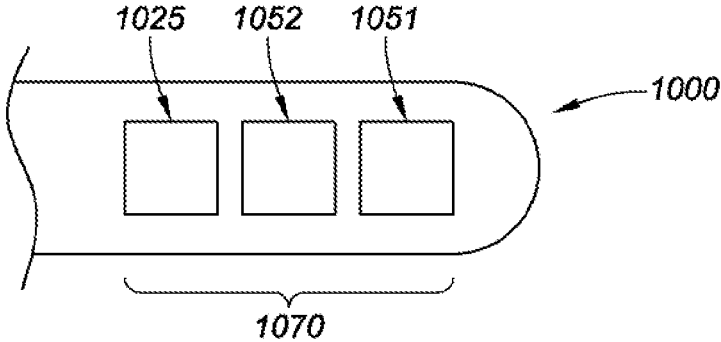
FIG. 10 is a top view of a catheter tip including a force sensor, consistent with various aspects of the present disclosure.

FIG. 10 is a top view of a catheter tip 1000 including a force sensor system 1070. In one specific embodiment, a deformable body 1025 may be proximal to both a magnetic sensor 1052 (coupled to a static portion of the deformable body) and a permanent magnet 1051 (coupled to a dynamic portion of the deformable body). The permanent magnet is located distal of the magnetic sensor. In such an embodiment, the magnetic sensor 1052 is extended over the deformable body 1025 via a beam. In other embodiments, a mirror image of the above configuration is also envisioned. Specifically, the deformable body may be distal both the magnetic sensor and the permanent magnet, and the magnet is coupled to a beam that extends proximally from a dynamic portion of the deformable body toward a magnetic sensor on the static portion of the deformable body. Other example embodiments may readily interchange the positioning of the magnetic sensor, permanent magnet, and deformable body.

Aspects of FIGS. 7-10 are further directed to a tunable lateral/axial compliance ratio to achieve a desirable axial force sensitivity at low lateral deformation of the deformable body. One method to achieve a desirable lateral/axial compliance ratio is to implement a beam that is coupled to a distal (dynamic) portion of the deformable body and that extends proximally (and co-axially) toward a magnetic sensor. A permanent magnet is coupled to the proximal end of the beam and the interaction between the magnetic sensor and the permanent magnet facilitates force sensing. See, e.g., FIGS. 7A-C. In further more specific embodiments, the beam and permanent magnet may be hollow to allow an irrigant lumen, for example, to pass through the force sensor system to a distal end of a catheter.

One example embodiment of the magnetic sensor, discussed herein, may be a Hall effect chip (also referred to as a Hall effect sensor) including receivers directed at magnetic fields received from all three-axis (x, y, z). In some embodiments consistent with the present disclosure, it may be desirable to have an at-rest position of the receivers, within the Hall effect chip, relative to the center of a permanent magnet of approximately 1.5 millimeters. As disclosed in detail above, various aspects of the present disclosure are directed to the proximal positioning of the magnet and magnetic sensor relative to a deformable body.

To fine tune a measured lateral deflection of a deformable body, a permanent magnet may be longitudinally extended by a beam that extends over the deformable body. The longer the beam, the larger the lateral deflection of the permanent magnet in response to a force exerted on a catheter tip. Where desirable, the length of the beam may be selected to facilitate a 1:1 ratio between a resulting measured deflection of the deformable body in response to a lateral force and an equivalent axial force on the catheter tip.

To simplify a force sensor system consistent with the present disclosure, a permanent magnet may be substituted for an electromagnet that does not require a power source and corresponding wiring to produce a magnetic field. However, in such an embodiment, the permanent magnet substitute may not produce an equivalent magnetic field. As a result, such embodiments require closer proximity between a magnetic sensor and the permanent magnet by extending the permanent magnet over a deformable body via a beam.

Magnetic sensors as discussed herein may be susceptible to noise associated with the Earth's magnetic field. Specifically, in some embodiments, the sensed magnetic field changes received from the permanent magnet in response to a deformation of the deformable body may be relatively small compared to Earth's magnetic field. Accordingly, shielding the magnetic sensor from the Earth's magnetic field may help to reduce the signal-to-noise ratio due to the Earth's magnetic field. However, such shielding may impede the use of catheter localization systems. Alternatively (or in combination with the above embodiment), a relative static position of the magnetic sensor relative to the permanent magnet may be reduced to increase the strength of the sensed magnetic field. However, such an embodiment may reduce the available sensing range of the force sensor.

In more specific embodiments, to solve the above mentioned noise problem in the magnetic sensor signal, a secondary magnetic sensor located proximal to the first magnetic sensor and outside of the magnetic field of the permanent magnet may be utilized. The secondary magnetic sensor picks up the Earth's magnetic field, slightly altered but in a constant manner, by the permanent magnet. The magnetic field changes of the permanent magnet relative to the secondary magnetic sensor are limited by the deformation of the deformable body, the relatively large distance between the permanent magnet and the secondary magnetic sensor, and the low magnetic-field gradients therebetween. Accordingly, the magnetic field from the permanent magnet in proximity to the secondary magnetic field is substantially constant. Back-end processing circuitry may receive both the signals from the first and secondary magnetic sensor, and filter out the Earth's magnetic field signal from the first magnetic sensor's signal to improve the signal-to-noise ratio-thereby facilitating improved force sensor measurements.

In embodiments where a first and secondary magnetic sensor can be located at a sufficient physical distance from one another to facilitate the secondary magnetic sensor picking-up an unadulterated signal from the Earth's magnetic field (i.e., unadulterated by a permanent magnet, or from any other ambient field), then the system may actively compensate for the Earth's magnetic field and filter-out artefacts sensed by the first magnetic sensor. Specifically, if the ambient field is known (as supplied by the secondary magnetic sensor), it may be subtracted from the primary sensor signal, thus correcting for the ambient field artefact effect on the computed force. Accordingly, an improved force calculation may be determined by the system. In some more specific embodiments, the physical distance, between the permanent magnet and the secondary magnetic sensor, may be in excess of 10 millimeters. Even at a distance of 10 millimeters, the field of the permanent magnet acting on the secondary magnetic sensor may be non-zero. At less than a 10 millimeter distance, a variation of the field resulting from simple force sensing (compliance of the deformable body) will not be negligible. At 5 millimeters distance (between the permanent magnet and the secondary magnetic sensor), for instance, a 100 g load on the deformable body will cause a field change at the secondary magnetic sensor that is approximately the same as Earth's magnetic field. As a result, the secondary magnetic sensor will not detect the value to be subtracted (ambient field), but a sum of that value and a portion of the magnetic field of the permanent magnet. In some embodiments, shielding the secondary magnetic sensor from the permanent magnet field may not be desirable, as the shielding would also shield the ambient (Earth) field from the secondary magnetic sensor. Accordingly, various embodiments may require a distance which is large enough so that variation of the magnetic field from the permanent magnet under the effect of a force, as sensed by the secondary magnetic sensor, is weak, and that in many configurations requires about 10 millimeters of distance between the permanent magnet and the secondary magnetic sensor.

In embodiments where a first and secondary magnetic sensor cannot be located at a sufficient physical distance from one another to facilitate the secondary magnetic sensor picking-up an unadulterated signal from the Earth's magnetic field, a partial compensation can be made by estimating the vector field value of the permanent magnetic field at the location of the secondary magnetic sensor from the output signal of the primary magnetic sensor. The difference between the two signals is a good estimation of the ambient field. The ambient field may then be used to correct the first magnetic sensor value (this is similar, at least conceptually, to using Newton's method to approximate a solution of an equation). As an example, at low forces, the permanent magnetic field change at the secondary magnetic sensor is low. In response, the secondary magnetic sensor picks a relatively unadulterated ambient field, which can then be subtracted. The sensor accuracy is given as a percentage of sensed force. This solution still maintains relatively little error as it subtracts a known error from a small force value—where the ambient field, which does not depend on the sensed force, is an additive, external field. In such embodiments, to determine the static field of the permanent magnet on the secondary magnetic sensor, a measurement of the field as sensed by the secondary magnetic sensor may be done at production level, for example, in a shielded chamber (no ambient field).

In one specific embodiment of a force sensing system utilizing two or more magnetic sensors, a distance between a permanent magnet and a first magnetic sensor is about 0.5 mm. The total motion (stroke) of the permanent magnet from its original position is about 0.1 mm (100 um) from its original position, in all 3 axial directions. In one example deformable body consistent with the present disclosure, compliance of the deformable body is about 50 microtesla/gram ("μT/gram") sensitivity for the axial load, and about 20 μT/gram for the lateral loads. Where the magnetic sensor is a Hall effect sensor, the sensor is indiscriminant of all the external fields in proximity to the sensor. However, portions of the resulting sensed magnetic field may be unrelated to the applied force on the catheter tip and the resulting relative motion between the magnet and the Hall effect sensor. Accordingly, as the Hall effect sensor is indiscriminate to magnetic fields in proximity to the sensor, a portion of the resulting signal is indicative of a change in orientation of the sensor in space (due to the Earth's magnetic field). The Earth's magnetic field is in the order of approximately 60 μT (but in some cases up to 100 T). In view of the sensitivity of the Hall effect sensor and the deformable body to a force exerted on the catheter tip, parasitic force reading variations may be approximately 2-5 grams of force variation (and as much as 7 grams) when the catheter is rotated in space, for example. This is because the Earth's magnetic field is approximately 2 to 5× larger than the sensitivity per gram of the force sensing system disclosed above. This problem may be solved by adding adequate shielding, but this may be problematic. Indeed, the catheter is tubular in nature, and magnetic shielding needs ideally "closed" enclosures. Various aspects of the present disclosure include the force sensing system, among other components, to enter and exit the tubular shielding. Alternatively, an active filtering approach may be implemented. A Hall effect sensor controller may control one or more sensors on the same digital line. Accordingly, an additional sensor may be positioned proximal the first sensor along the catheter shaft and may be used to identify and filter out portions of the digital signal associated with the Earth's magnetic field, among other transient magnetic fields.

Hall effect sensors as discussed herein may be either analog or digital devices. Moreover, the Hall effect sensors may or may not include 3-dimensional concentrators ("3-D concentrators"). A 3-D concentrator may facilitate a 2-dimensional chip form factor (also referred to as a flat chip design) by internally deviating the magnetic field components received by the Hall effect sensor. Specifically, the 3-D concentrator deviates the magnetic field components which are in a geometrical plane with the Hall effect sensor into a normal configuration with one or more Hall plates of the sensor. In other words, flux density parallel to an integrated chip surface (e.g., lateral and horizontal) of the Hall effect sensor is converted into orthogonal (e.g., vertical) components suitable for reception by the Hall plates within the sensor. The 3-D concentrator facilitates planar disposition of the Hall plates within the Hall effect sensor, as all the fields need not be received normal to the sensor. However, as a result of the 3-D concentrator, the maximum parallel field strength that the Hall effect sensor is capable of measuring may be limited to values such as 30-50 millitesla ("mT"); whereas a Hall effect sensor sans a 3-D concentrator may not be subject to an upper limit for magnetic field sensing (or the upper sensing limit is much higher, for example, 1 Tesla). Moreover, the 3-D concentrator may also be subject to remnant magnetization in response to magnetic field exposure greater than, for example, 1 Tesla. Such excess exposure may render the Hall effect sensor with 3-D concentrator inoperable.

In some specific embodiments of Hall effect sensors including 3-D concentrators, the 3-D concentrator may cause deviation of magnetic fields along an x-axis and y-axis, while magnetic fields along a z-axis are not affected by the 3-D concentrator. In the present embodiment, the magnetic field along the z-axis would already be normal relative to a Hall plate of the sensor.

Various other embodiments of Hall effect sensors, consistent with the present disclosure, may not include a 3-D concentrator, but instead may utilize natively, orthogonally disposed Hall plates within the sensor. Accordingly, such a sensor is not susceptible to magnetic field exposure limits, or remnant magnetization.

In catheter force sensing systems including dual magnetic sensor embodiments, the second sensor must be positioned outside of the permanent magnet's magnetic field (or at least far enough away that what the second sensor picks up from the magnet field is near constant). Far away from a magnet, the magnetic field is not only weaker, but the gradient is very weak when the magnet is moved due to forces on the catheter tip. The two magnetic sensors may be coupled to the same rigid part to guarantee static position and orientation with respect to one another. With such a configuration, the magnetic field detected by the second magnetic sensor is isolated to an external field, which affects both sensors. The external field may be subtracted from the signal obtained by the first magnetic sensor, making the latter signal much more independent from the external field. Accordingly, while the external field is present and sensed by both the magnetic sensors, the filtered signal for the first magnetic sensor is devoid of such an external field.

In one specific embodiment, where a first and second magnetic sensor are positioned 5 mm away from one another, the magnetic radial field sensed by the second magnetic sensor will show <10 μT variation in response to relative motion of the magnet. Accordingly, the Earth field may be filtered from the radial field sensed by the first magnetic sensor quite reliably, reducing the initial Earth field induced error from 100 μT/20 μT/g=5 grams to 10 μT/20 μT/g=0.5 grams. In other embodiments consistent with the above, and which exhibit acceptable initial Earth field induced error, the second magnetic sensor may be positioned 2.5 mm away from the first magnetic sensor. The resulting force sensor system having a total rigid distal length of 15 millimeters. Beyond the Earth field, surgical suites may have other transient and ambient magnetic fields (e.g., computer systems, localization systems, magnetic resonance imaging systems). It has been discovered that the stronger the magnetic disturbance is, the more effective the above disclosed compensation scheme, since the magnetic field impacts both magnetic sensors proportionally.

U.S. Pat. No. 8,048,063 teaches various structures for reducing a trans-axial/axial compliance ratio of a deformable body. U.S. Pat. No. 8,048,063 is incorporated by reference, as though fully disclosed herein.

Figure 11A:
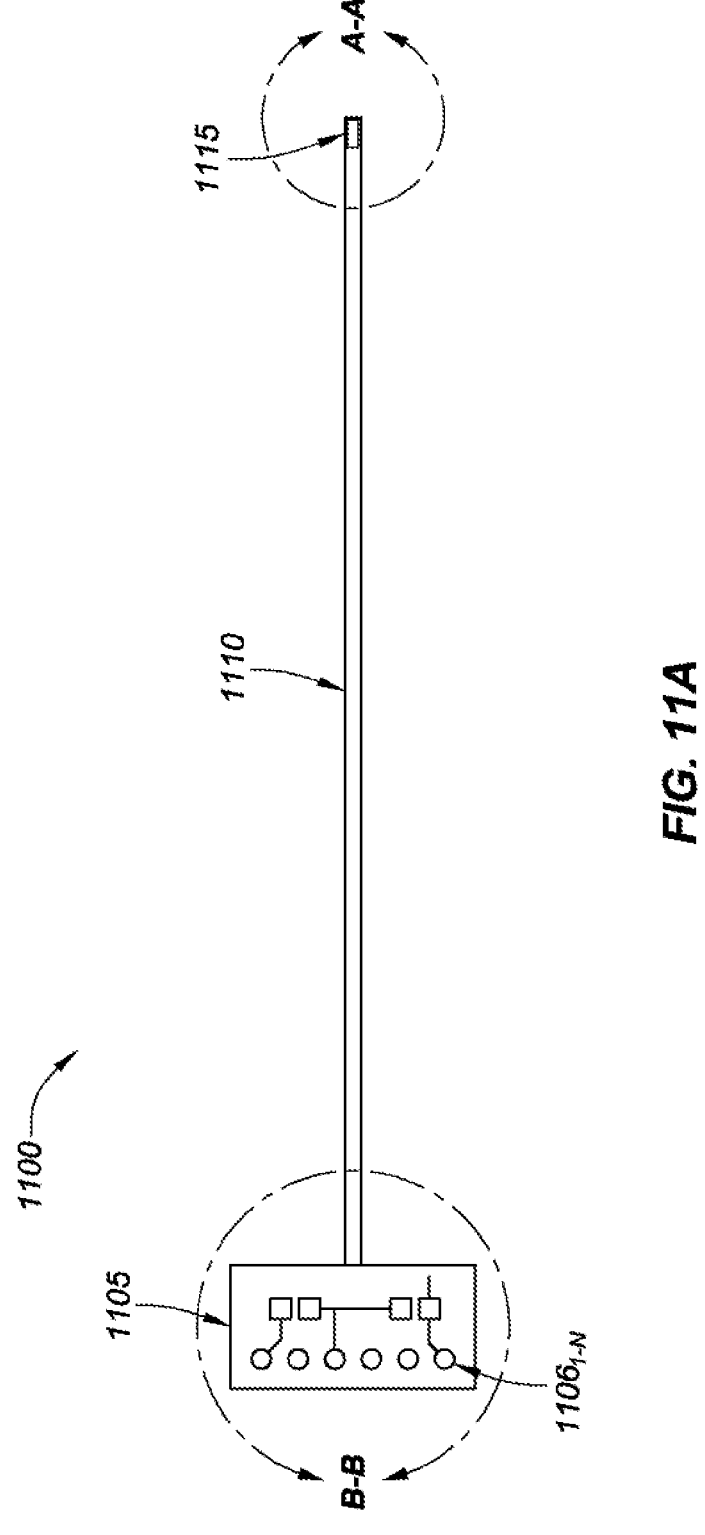
FIG. 11A is a top view of a magnetic sensor circuit board assembly, consistent with various aspects of the present disclosure.

FIG. 11A is a top view of a magnetic sensor circuit board assembly 1100 (also referred to as a digital Hall probe circuit assembly), consistent with various aspects of the present disclosure. FIGS. 11A-D are indicative of a one specific experimental embodiment. As shown in FIG. 11A, the magnetic sensor circuit board assembly 1100 includes a distal portion 1115 with a magnetic field sensor, this portion may be installed within, or near, a distal tip of an intravascular catheter, for example. An intermediate portion 1110 includes traces that communicate electrical signals indicative of a force exerted on a catheter tip from the distal portion 1115 to a proximal portion 1105. In some embodiments, the intermediate portion 1110 is a flexible circuit, rigid printed circuit board, conductive wires, or a combination thereof. The intermediate portion 1110 may extend a length of the catheter shaft. The proximal portion 1105 includes solder pads $1106_{1-N}$ that are electrically coupled to the magnetic field sensor at the distal portion 1115 of the magnetic sensor circuit board assembly 1100 via the electrical traces that extend through the intermediate portion 1110.

Figures 11B, 11C, 11D:
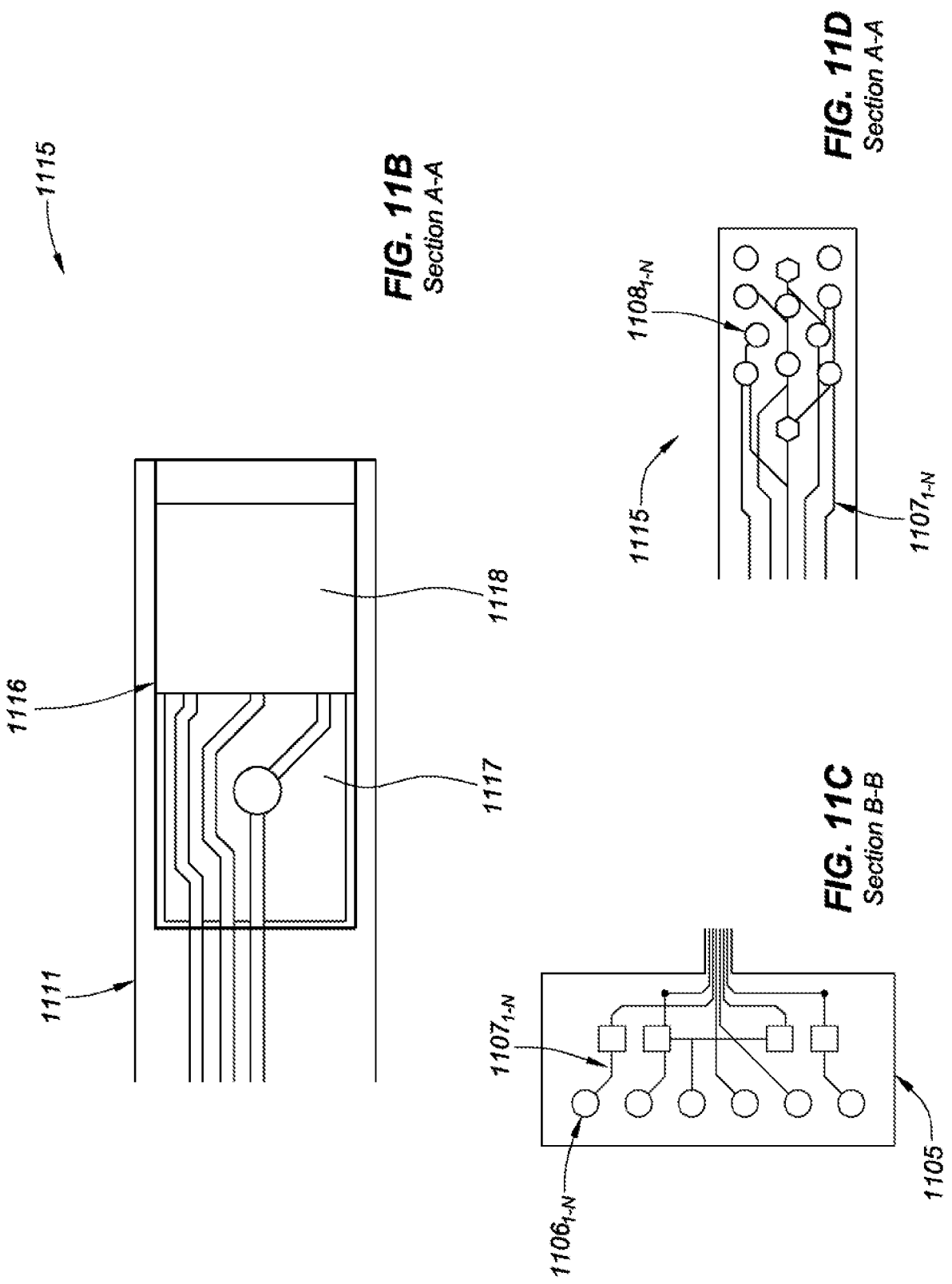
FIG. 11B is a top view of a magnetic sensor at a distal end of the magnetic sensor circuit board assembly of FIG. 11A, consistent with various aspects of the present disclosure.
FIG. 11C is a top view of a proximal portion of the magnetic sensor circuit board assembly of FIG. 11A, consistent with various aspects of the present disclosure.
FIG. 11D is a top view of a distal portion of the magnetic sensor circuit board assembly of FIG. 11A sans magnetic sensor, consistent with various aspects of the present disclosure.

FIG. 11B is a top view of a magnetic sensor 1118 (e.g., digital Hall effect probe) at a distal portion 1115 of the magnetic sensor circuit board assembly of FIG. 11A, consistent with various aspects of the present disclosure. As shown in FIG. 11B, the distal portion 1115 is coupled both mechanically and electrically to an intermediate portion 1111. The force sensor 1118 may be pre-packaged on a sub-assembly 1116 before the entire sub-assembly 1116 is mounted and electrically coupled to the distal portion 1115. The sub-assembly 1116 may include a rigid printed circuit board 1117 (flexible circuit, or other substrate) which facilitates mounting and electrically coupling a force sensor 1118 thereto—this process may be completed using a solder re-flow process, automated soldering, manual soldering, etc. During assembly of the magnetic sensor circuit board assembly of FIG. 11A, the sub-assembly 1116 may be mounted to, and electrically coupled with, a distal portion 1115 of the assembly. The coupling of the distal portion 1115 to the sub-assembly 1116 may include, for example, solder reflow on one or both, among other techniques well known in the art.

FIG. 11C is a top view of a proximal portion 1105 of the magnetic sensor circuit board assembly of FIG. 11A, consistent with various aspects of the present disclosure. As shown in FIG. 11C, the proximal portion 1105 includes a plurality of electrical traces 11071-N that run in and/or along a surface of the magnetic sensor circuit board. The electrical traces 11071-N electrically couple the force sensor at a distal portion of the circuit board assembly to solder pads/wire contacts $1106_{1-N}$. As discussed above, the intermediate portion and proximal portion 1105 may extend a length of a catheter shaft. In such a case, the solder pads $1106_{1-N}$ may be directly coupled to controller circuitry, or the solder pads $1106_{1-N}$ may be electrically coupled to lead wires (or another flexible circuit) that extend a remaining length of the catheter shaft. After the lead wires are coupled to the solder pads/wire contacts $1106_{1-N}$, the proximal portion 1105 may be rolled along a longitudinal axis of the catheter and inserted within a catheter shaft. In other embodiments, the proximal portion 1105 may be coupled to an outer diameter of a catheter shaft and covered with a nitinol jacket, for example. Various types of flexible and/or conductive trace-type circuits may be implemented in the embodiments disclosed herein, for example such as those described in U.S. patent application Ser. No. 15/115,228, which is incorporated by reference in its entirety as though fully disclosed herein.

FIG. 11D is a top view of a distal portion 1115 of the magnetic sensor circuit board assembly of FIG. 11A without a magnetic sensor assembled thereon. The distal portion 1115 includes electrical traces 11071-N which extend a length of the circuit board assembly and are electrically coupled to solder pads 11081-N. The solder pads 11081-N may be configured in a pattern which coincides with contacts on an underside of a chip. In some specific embodiments, the chips may be packaged in wafer level-chip sized packaging (also referred to as a "WL-CSP" chip). The chip and solder pads 11081-N may then be electrically/mechanically coupled via solder re-flow, manual soldering, etc.

Figure 12:
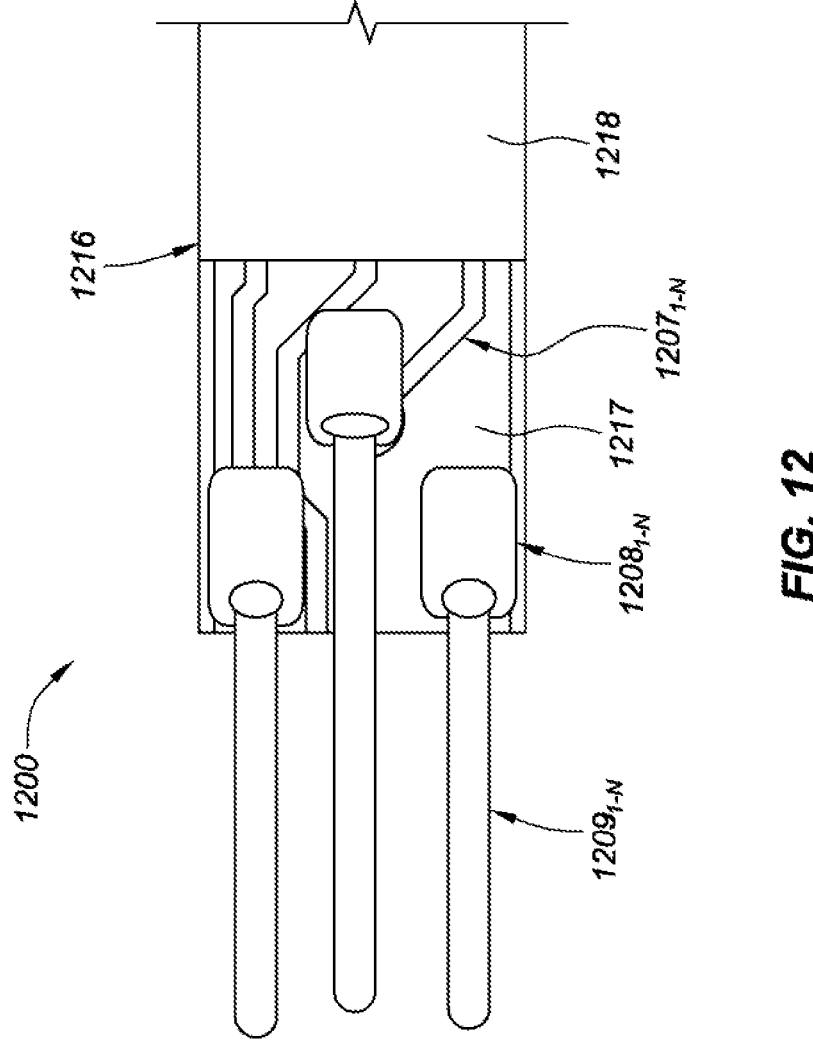
FIG. 12 is a partial top view of a magnetic field sensor circuit, consistent with various aspects of the present disclosure.

FIG. 12 is a top view of a magnetic field sensor circuit 1200, consistent with various aspects of the present disclosure. In the present embodiment, the flexible circuit of FIGS. 11A-D is replaced with lead wires. The magnetic sensor circuit 1200 includes a magnetic sensor subassembly 1216 that is coupled to lead wires 12091-N. The subassembly 1216 may be coupled to lead wires 12091-N via solder pads 12081-N. The subassembly 1216 further including a rigid printed circuit board 1217 that is mechanically and electrically coupled to magnetic sensor 1218 (such as a digital Hall effect probe) with electrical traces 12071-N coupling contacts on the magnetic sensor 1218 with the solder pads 12081-N and thereby the lead wires 12091-N.

Various figures of the present disclosure are shown with transparency to facilitate an understanding of the embodiments disclosed therein; for example, FIGS. 1, 4A-D, 6A-C, and 7A.

Specific/Experimental Force Sensor Calibration Methods

Aspects of the present disclosure are directed to specific/experimental embodiments directed to calibration of a force sensing system. In one specific/experimental embodiment of calibration for a force sensing system, a linear transfer matrix inversion is utilized. The linearity of the transfer matrix inversion may be conditioned on one or both of the mechanical linearity of a deformable body, and quasi-linearity of a magnetic field exerted in the stroke of the magnetic sensor (relative to the permanent magnet emitting the magnetic field and any other tertiary fields in proximity, e.g., Earth's magnetic field). In some implementations of the magnetic field sensor disclosed herein, it is desirable to limit the non-linear aspects of the magnetic field within the stroke (e.g., less than 100 μm) of the magnetic field sensor system. While a magnetic field is inherently non-linear, the calibration transfer matrix inversion may be essentially linear due to the small scale at which the magnetic field is monitored (e.g., less than 0.1 mm).

Figure 13:
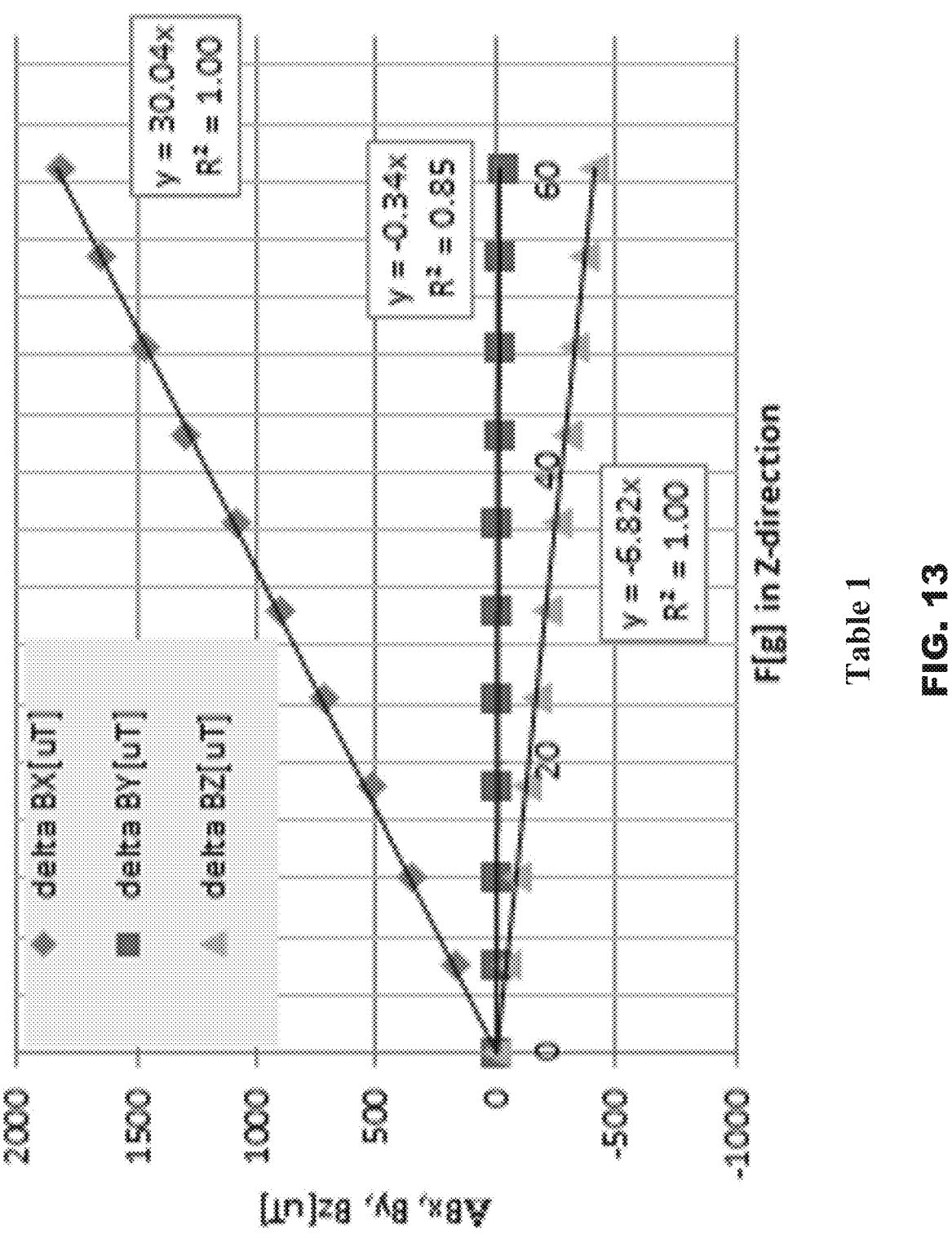
FIG. 13 contains Table 1 depicting the force vs. magnetic field (sensed in three axes).

In one example calibration process, a force is exerted along a single axis of a force sensor and the resulting magnetic field measured by the magnetic sensor. The force vs. magnetic field (sensed in three axes) is presented in Table 1 depicted in FIG. 13. It is important to note in Table 1 that the z-axis of the catheter is aligned with the x-axis of the magnetic field sensor.

As shown in Table 1, while the measurement axis (delta Bx) of the magnetic sensor (aligned with the axis upon which the force is exerted) produces a linear signal output associated with the force exerted, a transverse measurement axis (delta Bz) of the magnetic sensor also detects a change in the magnetic field which is a false indication of a force exerted laterally on the force sensor system. The sensed magnetic field data is then used to populate a calibration matrix (A) which is inversed. The inversed calibration matrix ($A^{-1}$) may then be input to a Force equation:

$$\vec{F} = A^{-1} \cdot \vec{\Delta B}$$

where $$(\vec{\Delta} = A \cdot \vec{F}) \qquad \text{Equation 1}$$

After calibration, the resulting magnetic field measured by the magnetic sensor becomes the values depicted in Table 2.

Figure 14:
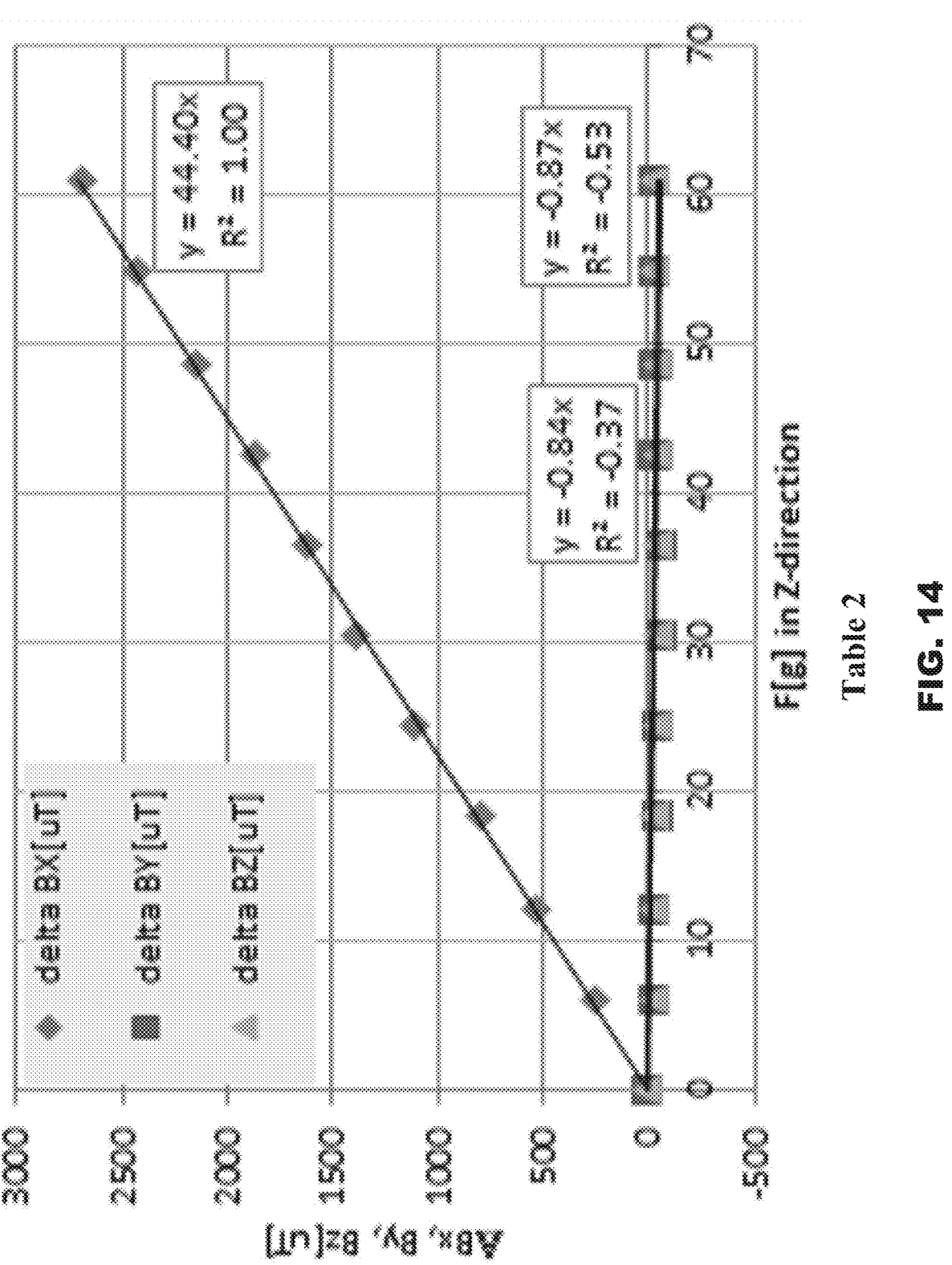
FIG. 14 contains Table 2 depicting the exerted force on the force sensor system.
Figure 15:
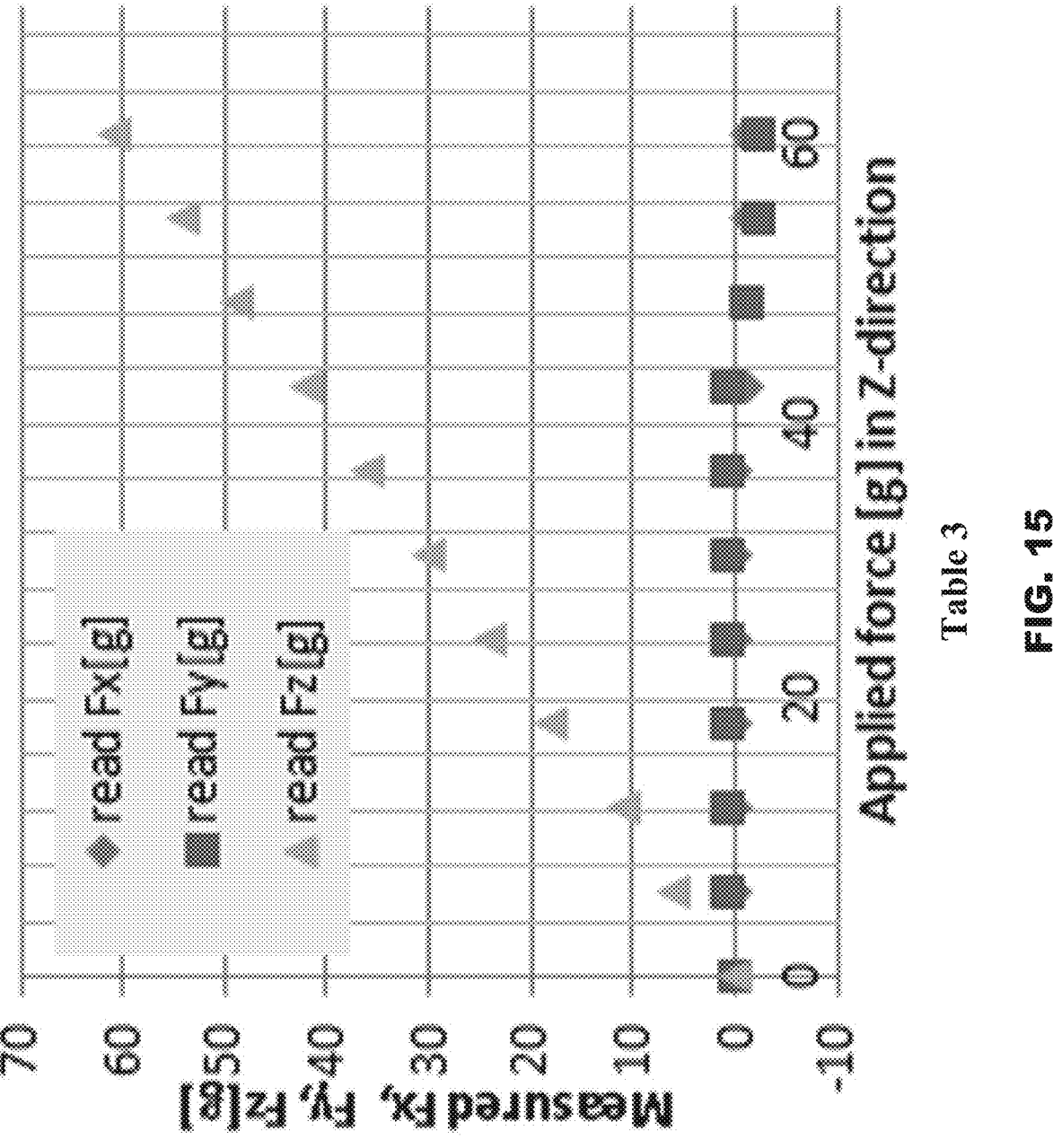
FIG. 15 contains Table 3 depicting the direct correlation between the exerted force and the sensed force after the calibration matrix is determined and applied to the acquired magnetic field data.

Applying Equation 1 to the data of Table 1, the exerted force on the force sensor system is accurately output while mitigating false indications in Table 2 depicted in FIG. 14. Table 3 depicted in FIG. 15 shows the direct correlation between the exerted force and the sensed force after the calibration matrix is determined and applied to the acquired magnetic field data.

The above described calibration process may be conducted simultaneously for all measurement axis, or each measurement axis may be calibrated individually.

After the calibration of each measurement axis of the force sensor is completed, one or more known forces may be applied to a deformable body of the force sensor to verify the calibration of the force sensor.

As disclosed in various embodiments, it was discovered that a magnetic sensor, in close proximity to a permanent magnet, may be susceptible to temperature-related signal drift; this is contrary to a magnetic sensor placed only in the presence of Earth's magnetic field which exhibits a temperature dependence in the range of approximately <1 $\mu$T/° C. for temperatures in the range of 25-65° C. However, with a permanent magnet in close proximity to the magnetic sensor, it has been discovered that temperature dependence is quite high. Temperature dependence may be at least partially due to the field strength variation of the permanent magnet over a temperature range. Without a thermal compensation calibration for the force sensor system, the resulting force calculation can have an error as high as 10 grams/1° C. The sensing drift of the magnetic sensor may be as high as 30 $\mu$T (approximately 50% of Earth's magnetic field). Moreover, the deformable body may also be susceptible to large temperature fluctuations (due to thermal expansion/contraction) which will affect the relative placement of the magnetic sensor and permanent magnet. As a result, many embodiments of the present disclosure (including ablation catheter applications) may benefit from the use of a thermal compensation calibration which corrects for all of these thermally induced factors. To facilitate thermal compensation calibration, a temperature sensor may be positioned within the distal portion of the catheter (e.g., near the permanent magnet and/or magnetic sensor), and in some embodiments the magnetic sensor may include an integrated temperature sensor integrated onto or within a chip package.

U.S. provisional application No. 61/915,212, filed 12 Dec. 2013 is hereby incorporated by reference as though fully set forth herein.

Although several embodiments have been described above with a certain degree of particularity to facilitate an understanding of at least some ways in which the disclosure can be practiced, those skilled in the art could make numerous alterations to the disclosed embodiments without departing from the scope of the present disclosure and the appended claims. It is intended that all matter contained in the above description or shown in the accompanying drawings shall be interpreted as illustrative only and not limiting. Accordingly, the examples and embodiments herein should not be construed as limiting the scope of the disclosure. Changes in detail or structure can be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments can be practiced without such specific details. In other instances, well-known operations, components, and elements cannot have been described in detail so as not to obscure the embodiments described in the specification. Those of ordinary skill in the art will understand that the embodiments described and illustrated herein are non-limiting examples, and thus it can be appreciated that the specific structural and functional details disclosed herein can be representative and do not necessarily limit the scope of the embodiments, the scope of which is defined solely by the appended claims. As one example, while various embodiments of the present disclosure are directed to deformable bodies including leaf springs, leaf springs are just one representative embodiment, and other compliant structures may also be utilized.

The terms "including," "comprising" and variations thereof, as used in this disclosure, mean "including, but not limited to," unless express specified otherwise. The terms "a," "an," and "the," as used in this disclosure, means "one or more," unless expressly specified otherwise.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics can be combined in any suitable manner in one or more embodiments. Thus, the particular features, structures, or characteristics illustrated or described in connection with one embodiment can be combined, in whole or in part, with the features, structures, or characteristics of one or more other embodiments without limitation.

Although process steps, method steps, algorithms, or the like, can be described in a sequential order, such processes, methods, and algorithms can be configured to work in alternative orders. In other words, any sequence or order of steps that can be described does not necessarily indicate a requirement that the steps be performed in that order. The steps of the processes, methods, and algorithms described herein can be performed in any order practical. Further, some steps can be performed simultaneously.

When a single device or article is described herein, it will be readily apparent that more than one device or article can be used in place of a single device or article. Similarly, where more than one device or article is described herein, it will be readily apparent that a single device or article can be used in place of the more than one device or article. The functionality or the features of a device can be alternatively embodied by one or more other devices which are not explicitly described as having such functionality or features.

It will be appreciated that the terms "proximal" and "distal" can be used throughout the specification with reference to a clinician manipulating one end of an instrument used to treat a patient. The term "proximal" refers to the portion of the instrument closest to the clinician and the term "distal" refers to the portion located furthest from the clinician. However, surgical instruments can be used in many orientations and positions, and these terms are not intended to be limiting and absolute. All other directional or spatial references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and can include intermediate members between a connection of elements and relative movement between elements. As such, joinder references do not necessarily infer that two elements are directly connected and in fixed relation to each other.

Various modules or other circuits can be implemented to carry out one or more of the operations and activities described herein and/or shown in the figures. In these contexts, a "module" is a circuit that carries out one or more of these or related operations/activities (e.g., ablation controller circuitry). For example, in certain of the above-discussed embodiments, one or more modules are discrete logic circuits or programmable logic circuits configured and arranged for implementing these operations/activities. In certain embodiments, such a programmable circuit is one or more computer circuits programmed to execute a set (or sets) of instructions (and/or configuration data). The instructions (and/or configuration data) can be in the form of firmware or software stored in and accessible from a memory (circuit). As an example, first and second modules include a combination of a CPU hardware-based circuit and a set of instructions in the form of firmware, where the first module includes a first CPU hardware circuit with one set of instructions and the second module includes a second CPU hardware circuit with another set of instructions.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A force sensing system for a medical catheter, the force sensing system comprising:

a deformable body in an ablation catheter tip, the deformable body including distal and proximal portions, an inner portion, and an outer portion coupled to a catheter shaft, the outer portion configured with a deformable zone that facilitates deflection in at least one spatial dimension in response to a force exerted on the distal portion of the ablation catheter tip;

a beam coupled to the distal portion of the deformable body, a first portion of the beam coupled to a sidewall of the catheter shaft and a second portion of the beam extending along a central axis of the proximal portion of the deformable body such that the central axis passes through the second portion of the beam;

a permanent magnet attached to a proximal end of the beam; and a magnetic field sensor attached to the deformable body opposite the permanent magnet relative to the deformable body, the magnetic field sensor configured to measure a change in magnetic field associated with a change in relative position of the magnetic field sensor and permanent magnet as the deformable body deflects, wherein dimensional aspects of the deformable body are configured with a tunable compliance ratio relative to the deflection of the deformable body in response to the force exerted on the distal portion of the ablation catheter tip, wherein the dimensional aspects of the deformable body include one or more compliant leaf springs, the one or more compliant leaf springs comprising at least one slit elongated in a circumferential direction about the deformable body, and wherein the magnetic field sensor is further configured and arranged to sense a magnetic field that varies based on the deflection of the one or more compliant leaf springs manipulating a relative distance between the magnetic field sensor and the permanent magnet.

2. The force sensing system of claim 1, further including controller circuitry communicatively coupled to the magnetic field sensor and configured and arranged to receive a signal from the magnetic field sensor indicative of the magnetic field sensed and associate the sensed magnetic field with the force exerted on the distal portion of the deformable body.

3. The force sensing system of claim 2, wherein the system further includes a second magnetic field sensor, the second magnetic field sensor is positioned outside of the magnetic field emitted by the permanent magnet and communicatively coupled to the controller circuitry, the second magnetic field sensor is configured and arranged to detect an ambient magnetic field and transmit a second signal to the controller circuitry indicative of the ambient magnetic field; and wherein the controller circuitry is further configured and arranged to sample the second signal and filter the second signal from the signal received from the magnetic field sensor.

4. The force sensing system of claim 1, wherein the deformable body is further configured and arranged to disassociate a directionality of the force exerted on the distal portion of the deformable body with a magnitude of the deformation of the deformable body.

5. The force sensing system of claim 1, wherein the deformable body further includes a deflectable portion between the proximal and distal portions, and both the permanent magnet and the magnetic field sensor are positioned on the same side of the deflectable portion of the deformable body.

6. The force sensing system of claim 1, wherein the deformable body further includes a deflectable portion between the proximal and distal portions, and the beam extends proximally over the deflectable portion; and wherein the permanent magnet is coupled to the distal portion of the deformable body via the beam.

7. The force sensing system of claim 1, wherein a distance between the permanent magnet and the magnetic field sensor is equal to or less than 0.5 millimeters.

8. The force sensing system of claim 1, wherein the deformable body further includes one or more deformation limiters configured and arranged to limit the deflection of the deformable body in response to the force exerted exceeding a yield strength of the deformable body.

9. The force sensing system of claim 1, wherein the magnetic field sensor is a digital Hall effect probe.

10. The force sensing system of claim 1, wherein the magnetic field sensor is further configured and arranged to sense a change in the magnetic field indicative of deflections of the deformable body of less than or equal to 0.1 millimeters.

11. The force sensing system of claim 1, wherein the permanent magnet is attached to the inner portion of the deformable body, and the magnetic field sensor is attached to the outer portion of the deformable body.

12. An electrophysiology ablation catheter comprising:
   an ablation catheter tip configured and arranged to conduct ablation therapy on tissue;
   a steerable catheter body;
   a deformable body coupling a proximal end of the ablation catheter tip and a distal end of the steerable catheter body, the deformable body including two or more tunable compliant leaf springs configured to cause deflection of the catheter tip relative to the steerable catheter body, each of the two or more tunable compliant leaf springs comprising at least one slit elongated in a circumferential direction about the deformable body, the deformable body further comprising an inner portion and an outer portion coupled to the steerable catheter body, the outer portion configured with a deformable zone that facilitates deflection in at least one spatial dimension;
   a beam coupled to the ablation catheter tip, a first portion of the beam coupled to a sidewall of the steerable catheter body and a second portion of the beam extending along a central axis of the proximal portion of the deformable body such that the central axis passes through the second portion of the beam;
   a permanent magnet attached to the proximal end of the beam; and
   a magnetic field sensor attached to the distal end of the steerable catheter body, and configured and arranged to sense a change in a magnetic field indicative of a deflection of the deformable body, wherein the change in the measurable characteristic varies based on the deflection of the one or more compliant leaf springs manipulating a relative distance between the magnetic field sensor and the permanent magnet,
   wherein the permanent magnet is configured to remain static in response to the deflection of the deformable body,
   wherein the ablation catheter tip is further configured and arranged to transfer a force exerted on the catheter trip to the deformable body during an ablation therapy,
   wherein dimensional aspects of the deformable body are configured with a tunable compliance ratio relative to the deflection of the deformable body.

13. The electrophysiology ablation catheter of claim 12, wherein both the permanent magnet and the magnetic field sensor are positioned on the same side of the deformable body.

14. The electrophysiology ablation catheter of claim 12, wherein the beam extends proximally over the deformable body, and wherein the permanent magnet is coupled to the ablation catheter tip via the beam.

15. The electrophysiology ablation catheter of claim 12, wherein the force is a vector sum of one or more force vectors acting on the ablation catheter tip, and the deformation of the deformable body, in response to the force, is independent of the vector sum of the force.

16. The electrophysiology ablation catheter of claim 12, wherein a distance between the permanent magnet and the magnetic field sensor is equal to or less than 0.5 millimeters.

17. The electrophysiology ablation catheter of claim 12, further including controller circuitry communicatively coupled to the magnetic field sensor, and configured and arranged to receive a signal from the magnetic field sensor indicative of the deflection of the deformable body and determine the force exerted on the ablation catheter tip.

18. The electrophysiology ablation catheter of claim 17, further including a second magnetic field sensor, the second magnetic field sensor is positioned outside of the magnetic field emitted by the permanent magnet and communicatively coupled to the controller circuitry, the second magnetic field sensor is configured and arranged to detect an ambient magnetic field and transmit a second signal to the controller circuitry indicative of the ambient magnetic field; and the controller circuitry is further configured and arranged to sample the second signal and filter the second signal from the signal received from the magnetic field sensor.

19. A force sensing system for a medical catheter, the force sensing system comprising:
   a deformable body in an ablation catheter tip, the deformable body including distal and proximal portions, and inner portion, and an outer portion coupled to a catheter shaft, the outer portion configured with a deformable zone that facilitates deflection in at least one spatial dimension, the deformable body configured to deflect in response to a force exerted on the distal portion of the ablation catheter tip;
   a beam coupled to the distal portion of the deformable body, a first portion of the beam coupled to a sidewall of the catheter shaft and a second portion of the beam extending along a central axis of the proximal portion of the deformable body such that the central axis passes through the second portion of the beam;
   a measurement element attached to a proximal end of the beam; and
   a measurement receiver attached to the deformable body opposite the measurement element relative to the deformable body, the measurement receiver configured to measure a change in a measurable characteristic generated due to a change in relative position of the measurement element and receiver as the deformable body deflects in response to the force exerted on the distal portion of the deformable body,
   wherein both the measurement element and receiver are positioned on the same side of the deformable body, and
   wherein dimensional aspects of the deformable body are configured with a tunable compliance ratio relative to the deflection of the deformable body,
   wherein the dimensional aspects of the deformable body include one or more compliant leaf springs, the one or more compliant leaf springs comprising at least one slit elongated in a circumferential direction about the deformable body, and
   wherein the measurement receiver is further configured and arranged to sense a change in the measurable characteristic that varies based on the deflection of the one or more compliant leaf springs manipulating a relative distance between the measurement receiver and the measurement element.

20. The force sensing system of claim 19, wherein the measurement element is a permanent magnet and the measurement receiver is a magnetic sensor.

21. The force sensing system of claim 19, wherein the beam extends proximally over the deformable body, wherein the measurement element is coupled to the distal portion of the deformable body via the beam.

22. The force sensing system of claim 19, wherein the measurement element is attached to the inner portion of the deformable body, and the measurement receiver is attached to the outer portion of the deformable body.

* * * * *